(12) United States Patent
Du

(10) Patent No.: US 11,517,417 B2
(45) Date of Patent: *Dec. 6, 2022

(54) WOVEN PROSTHESIS AND METHOD FOR MANUFACTURING THE SAME

(71) Applicant: MAQUET CARDIOVASCULAR LLC, Wayne, NJ (US)

(72) Inventor: George Du, Sparta, NJ (US)

(73) Assignee: MAQUET CARDIOVASCULAR LLC, Wayne, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/883,571

(22) Filed: May 26, 2020

(65) Prior Publication Data
US 2021/0007839 A1 Jan. 14, 2021

Related U.S. Application Data

(63) Continuation of application No. 16/013,778, filed on Jun. 20, 2018, now Pat. No. 10,682,221, which is a
(Continued)

(51) Int. Cl.
*A61F 2/00* (2006.01)
*A61F 2/02* (2006.01)
(Continued)

(52) U.S. Cl.
CPC ............ *A61F 2/06* (2013.01); *A61F 2/07* (2013.01); *A61F 2/90* (2013.01); *D03D 3/02* (2013.01);
(Continued)

(58) Field of Classification Search
CPC ........ A61F 2/07; A61F 2/90; A61F 2002/065; A61F 2250/0039; A61F 2250/0037; A61F 2/954; A61F 2230/0067; A61F 2250/0017; A61F 2250/001; A61F 2240/001; A61F 2230/001; A61F 2230/0017; A61F 2230/005; A61F 2230/0054; A61F 2/856; D10B 2509/06; D03D 3/02; D03D 3/06; D03D 15/00; D03D 49/68; D03D 11/02; D03D 13/00; D04C 1/06

See application file for complete search history.

(56) References Cited

U.S. PATENT DOCUMENTS 1,186,612 A 6/1916 Satinover
1,289,015 A 12/1918 Suter
(Continued)

FOREIGN PATENT DOCUMENTS

CA 1131402 A1 9/1982
CN 101610738 A 12/2009
(Continued)

OTHER PUBLICATIONS

US 7,905,914 B2, 03/2011, Goicoechea et al. (withdrawn)
(Continued)

*Primary Examiner* — Robert H Muromoto, Jr.

(57) ABSTRACT

A woven prosthesis, such as a woven vascular graft, woven from warp and weft yarns. Velour warp yarns forming the prosthesis are selectively incorporated into a base layer of the prosthesis so as to provide a bulbous section without compromising the porosity of the prosthesis.

13 Claims, 13 Drawing Sheets

Related U.S. Application Data continuation of application No. 15/221,801, filed on Jul. 28, 2016, now Pat. No. 10,010,401, which is a continuation of application No. 13/997,095, filed as application No. PCT/US2011/067002 on Dec. 22, 2011, now Pat. No. 9,402,753, which is a continuation of application No. 12/978,382, filed on Dec. 23, 2010, now Pat. No. 8,696,741.

(51) Int. Cl.

| | | |
|---|---|---|
| *D03D 3/02* | (2006.01) | |
| *A61F 2/06* | (2013.01) | |
| *A61F 2/07* | (2013.01) | |
| *D03D 3/06* | (2006.01) | |
| *D03D 49/68* | (2006.01) | |
| *D03D 13/00* | (2006.01) | |
| *A61F 2/90* | (2013.01) | |
| *D03D 25/00* | (2006.01) | |

(52) U.S. Cl.
CPC ............ *D03D 3/06* (2013.01); *D03D 13/008* (2013.01); *D03D 49/68* (2013.01); *A61F 2210/0076* (2013.01); *A61F 2230/0076* (2013.01); *A61F 2250/001* (2013.01); *A61F 2250/0039* (2013.01); *D10B 2401/10* (2013.01); *D10B 2509/06* (2013.01)

(56) References Cited

U.S. PATENT DOCUMENTS

| | | | |
|---|---|---|---|
| 1,998,306 A | * | 4/1935 | Brown .................. D03D 49/68 139/188 A |
| 2,978,787 A | | 4/1961 | Liebig |
| 2,998,030 A | | 8/1961 | Koppelman et al. |
| 3,016,068 A | * | 1/1962 | Felix ........................ D03D 3/06 139/11 |
| 3,096,560 A | | 7/1963 | Liebig |
| 3,316,557 A | | 5/1967 | Liebig |
| 3,669,157 A | | 6/1972 | Woodall et al. |
| 3,719,212 A | | 3/1973 | Emerson et al. |
| 3,805,301 A | | 4/1974 | Liebig |
| 3,853,462 A | | 12/1974 | Smith |
| 3,945,052 A | | 3/1976 | Liebig |
| 3,986,828 A | | 10/1976 | Hoffman et al. |
| 4,047,252 A | | 9/1977 | Liebig et al. |
| 4,193,137 A | | 3/1980 | Heck |
| 4,346,741 A | | 8/1982 | Banos et al. |
| 4,443,895 A | | 4/1984 | Lane |
| 4,512,761 A | | 4/1985 | Raible |
| 4,517,687 A | * | 5/1985 | Liebig ...................... A61F 2/06 428/36.1 |
| 4,530,113 A | | 7/1985 | Matterson |
| 4,567,075 A | | 1/1986 | Krawczyk |
| 4,624,822 A | | 11/1986 | Arru et al. |
| 4,695,280 A | | 9/1987 | Watanabe et al. |
| 4,706,670 A | | 11/1987 | Andersen et al. |
| 4,743,250 A | | 5/1988 | Kitagawa et al. |
| 4,771,518 A | | 9/1988 | LaPointe et al. |
| 4,816,028 A | | 3/1989 | Kapadia et al. |
| 4,839,215 A | | 6/1989 | Starling et al. |
| 4,842,575 A | | 6/1989 | Hoffman et al. |
| 4,867,173 A | | 9/1989 | Leoni |
| 4,892,539 A | | 1/1990 | Koch |
| 4,969,896 A | | 11/1990 | Shors |
| 4,994,072 A | | 2/1991 | Bhate et al. |
| 5,070,914 A | | 12/1991 | Fukuta et al. |
| 5,108,424 A | | 4/1992 | Hoffman et al. |
| 5,121,751 A | | 6/1992 | Panalletta |
| 5,127,919 A | | 7/1992 | Ibrahim et al. |
| 5,139,515 A | | 8/1992 | Robicsek |
| 5,147,400 A | | 9/1992 | Kaplan et al. |
| 5,156,619 A | | 10/1992 | Ehrenfeld |
| 5,178,630 A | | 1/1993 | Schmitt |
| 5,178,634 A | | 1/1993 | Ramos Martinez |
| 5,192,296 A | | 3/1993 | Bhate et al. |
| 5,197,977 A | | 3/1993 | Hoffman et al. |
| 5,217,495 A | | 6/1993 | Kaplan et al. |
| 5,246,445 A | | 9/1993 | Yachia et al. |
| 5,282,846 A | | 2/1994 | Schmitt |
| 5,282,847 A | | 2/1994 | Trescony et al. |
| 5,282,848 A | | 2/1994 | Schmitt |
| 5,314,443 A | | 5/1994 | Rudnick |
| 5,314,468 A | | 5/1994 | Ramos Martinez |
| 5,320,639 A | | 6/1994 | Rudnick |
| 5,370,682 A | | 12/1994 | Schmitt |
| 5,383,892 A | | 1/1995 | Cardon et al. |
| 5,383,925 A | | 1/1995 | Schmitt |
| 5,385,580 A | | 1/1995 | Schmitt |
| 5,413,597 A | | 5/1995 | Krajicek |
| 5,413,598 A | | 5/1995 | Moreland |
| 5,433,909 A | | 7/1995 | Martakos et al. |
| 5,445,599 A | | 8/1995 | Edenbaum |
| 5,456,711 A | | 10/1995 | Hudson |
| 5,465,762 A | * | 11/1995 | Farley .................... D03D 49/68 139/192 |
| 5,476,506 A | | 12/1995 | Lunn |
| 5,487,858 A | | 1/1996 | Schmitt |
| 5,496,364 A | | 3/1996 | Schmitt |
| 5,505,887 A | | 4/1996 | Zdrahala et al. |
| 5,509,931 A | | 4/1996 | Schmitt |
| 5,514,181 A | * | 5/1996 | Light ...................... A61L 27/48 623/13.18 |
| 5,522,881 A | | 6/1996 | Lentz |
| 5,522,883 A | | 6/1996 | Slater et al. |
| 5,527,353 A | | 6/1996 | Schmitt |
| 5,545,215 A | | 8/1996 | Duran |
| 5,556,426 A | | 9/1996 | Popadiuk et al. |
| 5,562,725 A | | 10/1996 | Schmitt et al. |
| 5,575,816 A | | 11/1996 | Rudnick et al. |
| 5,607,478 A | | 3/1997 | Lentz et al. |
| 5,611,127 A | | 3/1997 | Ceriani et al. |
| 5,628,786 A | | 5/1997 | Banas et al. |
| 5,647,848 A | | 7/1997 | Jorgensen |
| 5,653,746 A | | 8/1997 | Schmitt |
| 5,662,675 A | | 9/1997 | Stockert et al. |
| 5,665,114 A | | 9/1997 | Weadock et al. |
| 5,676,696 A | * | 10/1997 | Marcade .................. A61F 2/07 623/1.35 |
| 5,681,322 A | | 10/1997 | Hartigan, Jr. |
| 5,683,449 A | * | 11/1997 | Marcade .................. A61F 2/07 128/898 |
| 5,697,969 A | | 12/1997 | Schmitt et al. |
| 5,697,970 A | | 12/1997 | Schmitt et al. |
| 5,702,754 A | | 12/1997 | Zhong |
| 5,728,751 A | | 3/1998 | Patnaik |
| 5,732,572 A | | 3/1998 | Litton |
| 5,741,332 A | | 4/1998 | Schmitt |
| 5,741,881 A | | 4/1998 | Patnaik |
| 5,756,144 A | | 5/1998 | Wolff et al. |
| 5,769,884 A | | 6/1998 | Solovay |
| 5,772,864 A | | 6/1998 | Moller et al. |
| 5,800,510 A | | 9/1998 | Schmitt |
| 5,800,512 A | | 9/1998 | Lentz et al. |
| 5,800,514 A | * | 9/1998 | Nunez ...................... D03D 3/06 623/1.51 |
| 5,824,034 A | | 10/1998 | Schmitt et al. |
| 5,824,047 A | | 10/1998 | Moreland |
| 5,843,158 A | | 12/1998 | Lenker et al. |
| 5,843,166 A | | 12/1998 | Lentz et al. |
| 5,851,228 A | | 12/1998 | Pinheiro |
| 5,851,229 A | | 12/1998 | Lentz et al. |
| 5,851,230 A | | 12/1998 | Weadock et al. |
| 5,861,026 A | | 1/1999 | Harris et al. |
| 5,874,032 A | | 2/1999 | Zdrahala et al. |
| 5,877,263 A | | 3/1999 | Patnaik et al. |
| 5,891,195 A | | 4/1999 | Klostermeyer et al. |
| 5,904,714 A | * | 5/1999 | Nunez ...................... A61F 2/06 139/383 R |
| 5,906,639 A | | 5/1999 | Rudnick et al. |
| 5,906,641 A | * | 5/1999 | Thompson ................ A61F 2/90 623/1.15 |
| 5,910,168 A | | 6/1999 | Myers et al. |

(56) References Cited

U.S. PATENT DOCUMENTS

| | | | |
|---|---|---|---|
| 5,911,753 A | 6/1999 | Schmitt | |
| 5,913,894 A | 6/1999 | Schmitt | |
| 5,957,974 A * | 9/1999 | Thompson | A61F 2/90 |
| | | | 623/1.13 |
| 5,993,481 A * | 11/1999 | Marcade | A61F 2/07 |
| | | | 623/1.35 |
| 6,000,442 A | 12/1999 | Busgen | |
| 6,039,183 A | 3/2000 | Rudnick et al. | |
| 6,039,755 A | 3/2000 | Edwin et al. | |
| 6,042,592 A | 3/2000 | Schmitt | |
| 6,048,620 A | 4/2000 | Zhong | |
| 6,053,938 A | 4/2000 | Goldmann et al. | |
| 6,059,738 A | 5/2000 | Stoltze et al. | |
| 6,080,198 A | 6/2000 | Lentz et al. | |
| 6,086,968 A | 7/2000 | Horovitz | |
| 6,090,137 A | 7/2000 | Schmitt | |
| 6,096,525 A | 8/2000 | Patnaik | |
| 6,099,557 A | 8/2000 | Schmitt | |
| 6,136,022 A * | 10/2000 | Nunez | D03D 3/06 |
| | | | 623/1.1 |
| 6,148,865 A | 11/2000 | Head | |
| 6,159,239 A * | 12/2000 | Greenhalgh | A61F 2/07 |
| | | | 623/1.13 |
| 6,162,247 A | 12/2000 | Weadock et al. | |
| 6,176,875 B1 | 1/2001 | Lenker et al. | |
| 6,177,609 B1 | 1/2001 | Castro et al. | |
| 6,187,013 B1 | 2/2001 | Stoltze et al. | |
| 6,187,033 B1 | 2/2001 | Schmitt et al. | |
| 6,193,754 B1 | 2/2001 | Seedhom | |
| 6,237,644 B1 | 5/2001 | Hay et al. | |
| 6,250,193 B1 | 6/2001 | Head | |
| 6,309,343 B1 | 10/2001 | Lentz et al. | |
| 6,342,070 B1 | 1/2002 | Nguyen Thien Nhon | |
| 6,347,632 B1 | 2/2002 | Eberhardt et al. | |
| 6,352,554 B2 | 3/2002 | De Paulis | |
| 6,454,796 B1 * | 9/2002 | Barkman | A61F 2/07 |
| | | | 623/1.35 |
| 6,461,382 B1 | 10/2002 | Cao | |
| 6,478,817 B2 | 11/2002 | Schmitt et al. | |
| 6,482,228 B1 | 11/2002 | Norred | |
| 6,488,705 B2 | 12/2002 | Schmitt et al. | |
| 6,494,907 B1 | 12/2002 | Bulver | |
| 6,500,203 B1 * | 12/2002 | Thompson | A61F 2/07 |
| | | | 156/148 |
| 6,520,986 B2 | 2/2003 | Martin et al. | |
| 6,540,773 B2 | 4/2003 | Dong | |
| 6,544,285 B1 | 4/2003 | Thubrikar et al. | |
| 6,547,820 B1 | 4/2003 | Staudenmeier | |
| 6,554,855 B1 | 4/2003 | Dong | |
| 6,562,069 B2 | 5/2003 | Cai et al. | |
| 6,589,468 B1 | 7/2003 | Schmitt | |
| 6,592,615 B1 * | 7/2003 | Marcade | A61F 2/07 |
| | | | 623/1.16 |
| 6,596,023 B1 * | 7/2003 | Nunez | A61F 2/06 |
| | | | 623/1.3 |
| 6,613,072 B2 | 9/2003 | Lau et al. | |
| 6,626,938 B1 | 9/2003 | Butaric et al. | |
| 6,648,900 B2 | 11/2003 | Fleischman et al. | |
| 6,652,574 B1 | 11/2003 | Jayaraman | |
| 6,660,033 B1 * | 12/2003 | Marcade | A61F 2/07 |
| | | | 623/1.16 |
| 6,663,667 B2 | 12/2003 | Dehdashtian et al. | |
| 6,709,440 B2 | 3/2004 | Callol et al. | |
| 6,713,568 B1 | 3/2004 | Patnaik et al. | |
| 6,733,525 B2 | 5/2004 | Yang et al. | |
| 6,745,600 B2 | 6/2004 | Weiqing et al. | |
| 6,746,458 B1 | 6/2004 | Cloud | |
| 6,746,480 B2 | 6/2004 | Scholz et al. | |
| 6,749,628 B1 | 6/2004 | Callol et al. | |
| 6,783,554 B2 | 8/2004 | Amara et al. | |
| 6,783,556 B1 | 8/2004 | Gabbay | |
| 6,803,014 B2 * | 10/2004 | Ho | D04B 1/18 |
| | | | 264/488 |
| 6,803,069 B2 | 10/2004 | Patnaik et al. | |
| 6,821,294 B2 * | 11/2004 | Nunez | A61F 2/07 |
| | | | 623/1.3 |
| 6,840,958 B2 * | 1/2005 | Nunez | D03D 3/02 |
| | | | 623/1.3 |
| 6,875,230 B1 | 4/2005 | Morita et al. | |
| 6,883,522 B2 | 4/2005 | Spence et al. | |
| 6,887,268 B2 | 5/2005 | Butaric et al. | |
| 6,893,457 B2 | 5/2005 | Dong | |
| 6,939,372 B2 | 9/2005 | Dong | |
| 6,953,332 B1 | 10/2005 | Kurk et al. | |
| 6,964,679 B1 * | 11/2005 | Marcade | A61F 2/07 |
| | | | 623/1.13 |
| 6,994,724 B2 | 2/2006 | Schmitt | |
| 7,018,404 B2 | 3/2006 | Holmberg et al. | |
| 7,044,961 B2 | 5/2006 | Lentz et al. | |
| 7,160,323 B2 | 1/2007 | Pulnev et al. | |
| 7,169,189 B2 | 1/2007 | Bjarnason et al. | |
| 7,198,638 B2 | 4/2007 | Dong | |
| 7,309,461 B2 | 12/2007 | Kujawski et al. | |
| 7,314,483 B2 | 1/2008 | Landau et al. | |
| 7,419,502 B2 | 9/2008 | Pulnev et al. | |
| 7,431,733 B2 | 10/2008 | Knight | |
| 7,465,315 B2 | 12/2008 | Morris et al. | |
| 7,465,316 B2 | 12/2008 | Kujawski | |
| 7,491,231 B2 | 2/2009 | Nazzaro et al. | |
| 7,530,996 B2 | 5/2009 | Bentele et al. | |
| 7,550,006 B2 * | 6/2009 | Nunez | D03D 3/02 |
| | | | 623/1.51 |
| 7,618,447 B2 | 11/2009 | Case et al. | |
| 7,641,687 B2 | 1/2010 | Chinn et al. | |
| 7,682,381 B2 | 3/2010 | Rakos et al. | |
| 7,686,844 B2 | 3/2010 | Case et al. | |
| 7,717,952 B2 | 5/2010 | Case et al. | |
| 7,727,271 B2 | 6/2010 | Kujawski et al. | |
| 7,758,633 B2 | 7/2010 | Nazzaro | |
| 7,780,720 B2 | 8/2010 | Goicoechea et al. | |
| 7,806,920 B2 | 10/2010 | Duran | |
| 7,833,263 B2 | 11/2010 | Thistle | |
| 7,842,098 B2 | 11/2010 | Rioux et al. | |
| 7,857,845 B2 | 12/2010 | Stacchino et al. | |
| 7,862,604 B1 * | 1/2011 | Marcade | A61F 2/07 |
| | | | 623/1.13 |
| 7,862,609 B2 | 1/2011 | Butaric et al. | |
| 7,879,085 B2 | 2/2011 | Sowinski et al. | |
| 7,901,449 B2 | 3/2011 | Goicoechea et al. | |
| 8,177,839 B2 * | 5/2012 | Koob | A61L 27/24 |
| | | | 623/13.11 |
| 8,388,679 B2 * | 3/2013 | Du | A61F 2/06 |
| | | | 623/1.51 |
| 8,696,741 B2 * | 4/2014 | Du | A61F 2/90 |
| | | | 623/1.52 |
| 9,402,753 B2 * | 8/2016 | Du | A61F 2/90 |
| 10,010,401 B2 * | 7/2018 | Du | A61F 2/90 |
| 10,682,221 B2 * | 6/2020 | Du | A61F 2/06 |
| 2001/0049553 A1 | 12/2001 | De Paulis | |
| 2002/0035168 A1 | 3/2002 | Loomis et al. | |
| 2002/0040247 A1 | 4/2002 | Castro et al. | |
| 2002/0058991 A1 | 5/2002 | Schmitt | |
| 2002/0107561 A1 | 8/2002 | Pinheiro | |
| 2003/0078650 A1 | 4/2003 | Nunez | A61F 2/06 |
| | | | 623/36.1 |
| 2003/0109919 A1 | 6/2003 | Gantt et al. | |
| 2003/0130728 A1 | 7/2003 | Nunez et al. | |
| 2003/0163140 A1 | 8/2003 | Stoltze et al. | |
| 2003/0196717 A1 | 10/2003 | Nunez et al. | |
| 2003/0199992 A1 | 10/2003 | Schmitt et al. | |
| 2004/0019375 A1 | 1/2004 | Casey et al. | |
| 2004/0093065 A1 | 5/2004 | Yachia et al. | |
| 2005/0070994 A1 | 3/2005 | Sievers et al. | |
| 2005/0137677 A1 | 6/2005 | Rush | |
| 2005/0228487 A1 | 10/2005 | Kujawski | |
| 2005/0228488 A1 | 10/2005 | Nazarrao | |
| 2005/0228489 A1 | 10/2005 | Kujawski | |
| 2006/0178723 A1 | 8/2006 | Lentz | |
| 2008/0177379 A1 * | 7/2008 | Du | A61F 2/06 |
| | | | 623/1.51 |
| 2008/0275540 A1 | 11/2008 | Wen | |

(56) References Cited

U.S. PATENT DOCUMENTS

| | | | | |
|---|---|---|---|---|
| 2009/0126823 | A1* | 5/2009 | Yengkhom | D03D 37/00 139/450 |
| 2009/0177271 | A1 | 7/2009 | Fabiani | |
| 2009/0281614 | A1 | 11/2009 | Goldmann et al. | |
| 2010/0063576 | A1 | 3/2010 | Schaeffer et al. | |
| 2010/0094390 | A1 | 4/2010 | Goldmann et al. | |
| 2011/0112620 | A1* | 5/2011 | Du | D03D 3/06 623/1.1 |
| 2012/0165918 | A1* | 6/2012 | Du | A61F 2/90 623/1.15 |

FOREIGN PATENT DOCUMENTS

| | | |
|---|---|---|
| DE | 101 62 821 A1 | 6/2003 |
| DE | 102 42 154 A1 | 3/2004 |
| DE | 697 28 268 T2 | 1/2005 |
| DE | 102006062360 A1 | 6/2008 |
| DE | 102007013428 A1 | 9/2008 |
| DE | 202007018508 U1 | 9/2008 |
| EP | 0306690 A2 | 3/1989 |
| EP | 0692225 A2 | 1/1996 |
| EP | 0692264 A2 | 1/1996 |
| EP | 0955019 A2 | 11/1999 |
| EP | 1287790 A2 | 3/2003 |
| EP | 1340474 A2 | 9/2003 |
| EP | 0910310 B1 | 3/2004 |
| EP | 1935375 A1 | 6/2008 |
| EP | 2008615 A2 | 12/2008 |
| EP | 1935375 B1 | 3/2010 |
| ES | 2342431 T3 | 7/2010 |
| GB | 1173811 A | 12/1969 |
| GB | 1299963 A | 12/1972 |
| GB | 2070088 A | 9/1981 |
| JP | 03045743 A | 2/1991 |
| JP | 11-505296 A | 5/1999 |
| JP | H11505296 A | 5/1999 |
| JP | 2007532246 | 11/2007 |
| JP | 2007532246 A | 11/2007 |
| JP | 2010512867 A | 4/2010 |
| WO | 1995009585 A1 | 4/1995 |
| WO | 9940875 A1 | 8/1999 |
| WO | 1999040875 A1 | 8/1999 |
| WO | 01/52776 A1 | 7/2001 |
| WO | 2002024119 A1 | 3/2002 |
| WO | 2002102277 A2 | 12/2002 |
| WO | 2004021925 A2 | 3/2004 |
| WO | 2005067660 A2 | 7/2005 |
| WO | 2005099624 A1 | 10/2005 |
| WO | 2008/083767 A1 | 7/2008 |
| WO | 2008083767 A1 | 7/2008 |

OTHER PUBLICATIONS

Office Action issued in Japanese Application No. 2020088072 dated Jul. 20, 2021, 6 pages.
Jaksic, Danilo, et al., "Porosity of the Flat Textiles", Woven Fabric Engineering, (edited by Polona Dobnik Dubrovski), Aug. 2010, pp. 255-272.
Mathisen, Sven R., et al., "An experimental study of eight current arterial prostheses", Journal of Vascular Surgery, vol. 4, No. 1, Jul. 1986, pp. 33-41.
Wesolowski, Sigmund A., et al., "Porosity: primary determinant of ultimate fate of synthetic vascular grafts", Surgery, Jul. 1961, pp. 91-96.
Non-Final Office Action issued in U.S. Appl. No. 12/987,382, dated Nov. 8, 2012.
International Preliminary Report on Patentability issued in international Application No. PCT/US2011/067002, dated Jun. 25, 2013.
Non-Final Office Action issued in U.S. Appl. No. 13/997,095, dated Mar. 11, 2015.
Decision of Rejection issued in JP Application No. 2013-546439, dated Sep. 13, 2016.
Pre-trial Examination issued in JP Application No. 2013-546439, dated Mar. 14, 2017.
Non-Final Office Action issued in U.S. Appl. No. 15/221,801, dated Sep. 5, 2017.
Office Action issued in JP Application No. 2017-004444, dated Dec. 5, 2017.
Office Action issued in JP Application No. 2013-546439, dated Feb. 6, 2018.
Decision of Rejection issued in JP Application No. 2017-004444, dated Dec. 4, 2018.
Ragab A. et al., "Determination of Pore Size, Porosity and Pore Size Distribution of Woven Structures by Image Analysis Techniques", Journal of Textile Science & Engineering, vol. 7, No. 5, Sep. 2017, 9 pages.
Office Action from Japan Patent Office, dated Oct. 22, 2015 in relation to Japanese Patent Application No. 2013-546439, including English translation thereof.
Anderson, K. Suzanne., "Seamless Textiles with Inherent Shape" North Carolina State University, dated 2004, but not publicly accessible until Jan. 21, 2005 (see citation D6 of IDS), Thesis, cover page and index through p. 228.
Anderson, K et al. "Developing Seamless Shaped Woven Medical Products" Journal of Medical Engineering & Technology, May/Jun. 2004, vol. 28, No. 3, pp. 110-116.
Anderson, K. "Seamless Textiles with Inherent Shape," North Caroline State University, Jul. 2005, Dissertation, Abstract only (3 pages).
Written Search Report and Opinion for European Patent Application No. 07024710.1 (EP 1 935 375), published Mar. 18, 2008, including partial English machine translation.
Notice of Opposition to European Patent Application No. 07024710.1 (EP 1935 375), European Patent Office, Statement of Facts and Arguments from Opponent, Dec. 10, 2010 (date understood to be available at European Patent Office via EPO website, https://register.epo.org/application?number=EP07024710&lng=en&tab=doclist).
Cross, Will, Email dated Sep. 19, 2011.
Notice of Opposition to European Patent EP1935375 published by EPO (23 pages)—dated Dec. 10, 2010.
Submission of materials for opposition by opponent, Nov. 25, 2011 (2 pages).
European Patent Office, King, Dr. Martin W.—Letter to Tim Ashton, Nov. 25, 2011 (date understood to be available at European Patent Office via EPO website, https://register.epo.org/application?number=EP07024710&lng=en&tab=doclist).
Listing of items on the European Patent Register for EP1935375 indicating documents associated with the European Patent EP1935375, https://register.epo.org/application?Number=EP07024710&ing=en&tab-doclist, European Patent Office, as accessed by Applicant on Sep. 11, 2012.
European Patent Office, Abstract (one page) of Anderson Paper, Dec. 10, 2010 (date understood to be available at European Patent Office via EPO website, https://register.epo.org/application?number=EP07024710&lng=en&tab=doclist).
European Patent Office, Anderson Statement, Dec. 10, 2010 (date understood to be available at European Patent Office via EPO website, https://register.epo.org/application?number=EP07024710&lng=en&tab=doclist).
International Search Report and Opinion for PCT/US2011/67002, European Patent Office, dated May 4, 2012.
EPO communication dated Dec. 1, 2011 (1 page).
Reply from the opponent to submission of proprietor dated Nov. 25, 2011 (9 pages).
Reply of the patent proprietor to the notice(s) of opposition dated Jul. 19, 2011 (English translation not available) (24 pages).
Materials Cited in Opposition Request—(5 pages) (dated Dec. 10, 2010).
U.S. Appl. No. 12/387,201, filed Apr. 29, 2009, inventor is George Du.
U.S. Appl. No. 11/655,438, filed Jan. 19, 2007, inventor is George Du.
Hughes, G. Chad, Reimplantation Technique (David Operation) for Multiple Sinus of Valsalva Aneurysms, Ann Thorac Surg 2006; 82:e14-16.

(56) References Cited

OTHER PUBLICATIONS

Thubrikar, Mano J., Stress Sharing Between the Sinus and Leaflets of Canine Aortic Valve, Ann Thorac Surg, 1986;42:434-440.
Bentall, Hugh, A Technique for Complete Replacement of the Ascending Aorta, Thorax (1968) 23, 338-339.
Kunzelman, Karyn S., Surgery for Acquired Disease: Aortic root and valve relationships Impact on Surgical Repair, J. Thorac Cardiovasc. Surg 1994;107:162-170.
Bellhouse, B.J., Velocity and Pressure Distributions in the Aortic Valve, J. Fluid Mech. (1969), vol. 37, part 3, pp. 587-600, Great Britain.
Svensson, Lars G., Composite Valve Graft Replacement of the Proximal Aorta Comparison of Techniques in 348 Patients, Ann Thorac Surg 1992;54:427-439, 1992.
Cabrol, C., Complete Replacement of the Ascending Aorta with Reimplantation of the Coronary Arteries, J. Thorac Cardiovasc Surg. 81:309-315, 1981.
David, T. E., Feindel, C. M., Bos J.: Repair of the aortic valve in patients with aortic insufficiency and aortic root aneurysm. J Thorac Cardiovasc Surg 1995; 109(2):345-51.
David, T. E., Feindel, C. M., An Aortic Valve-Sparing Operation for Patients with Aortic Incompetence and Aneurysm of the Ascending Aorta, The Journal of Thoracic and Cardiovascular Surgery, vol. 103, 617-621, 1992.
David, Tirone E., Feindel, Christopher M., Surgery for Acquired Heart Disease, Repair of the aortic valve in patients with aortic insufficiency and aortic root aneurysm, J. Thorac Cardiovac Surg 1995;109:345-352, Canada.
Sarsam, M.A., Yacoub, M, Remodeling of the aortic valve annulus, The Journal of Thoracic and Cardiovascular Surgery, vol. 105, 435-438, 1993.
Bellhouse B. J.: The fluid mechanics of the aortic valve. In: Ionescu M. L., Ross D. N., Woller G. H., eds. Biological tissue heart replacement. London: Butterworth-Heinemann, 1972:32-8.
Richardt, Dorreen, A New Sinus Prosthesis for Aortic Valve-Sparing Surgery Maintaining the Shape of the Root at Systemic Pressure, Ann Thorac Surg, 2010; 89:943-946.
Office Action issued in connection with European Application No. 11808547.1, filed Dec. 22, 2011, dated Aug. 6, 2013, European Patent Office.
Response to Office in connection with European Application No. 11808547.1, filed Dec. 22, 2011, dated Feb. 14, 2014, European Patent Office.
Search Report issued in connection with European Application No. 11808547.1, filed Dec. 22, 2011, dated Jul. 12, 2012, European Patent Office.

\* cited by examiner

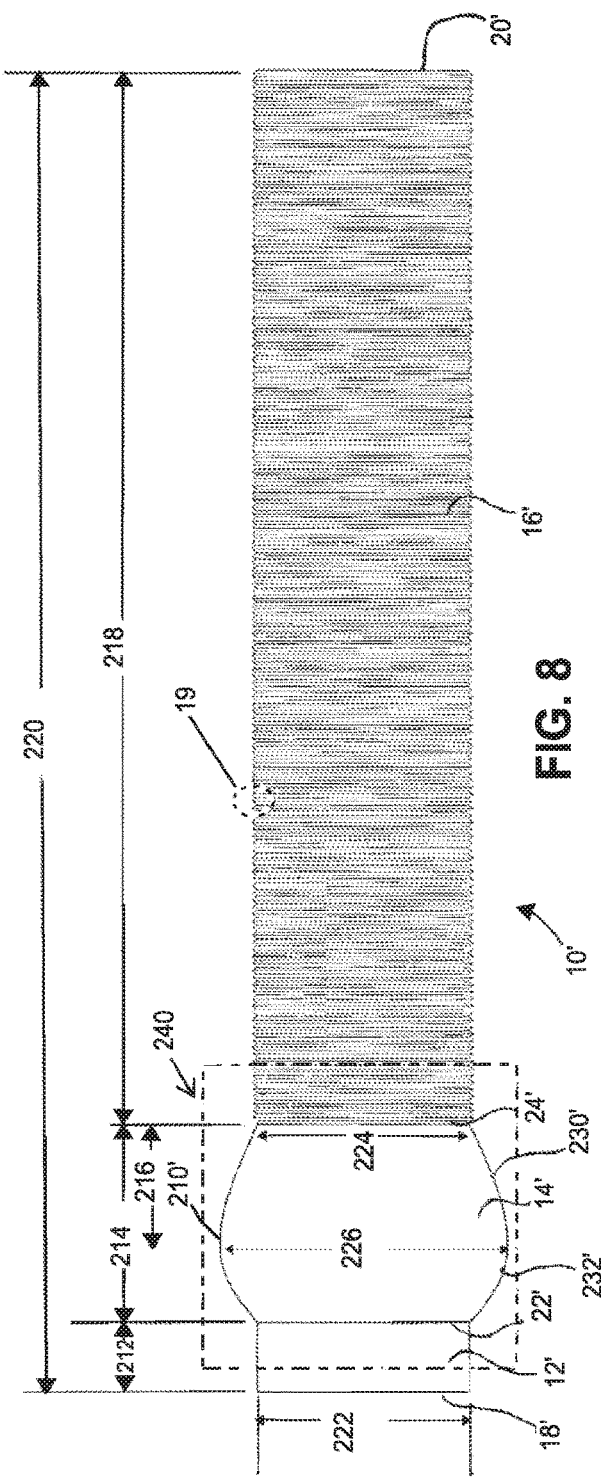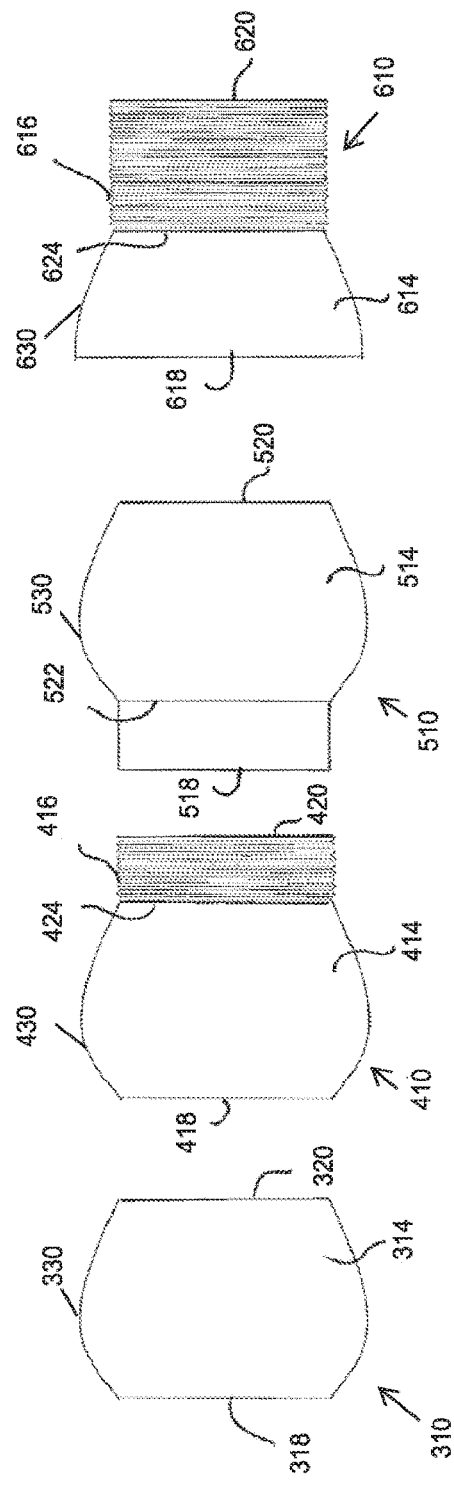

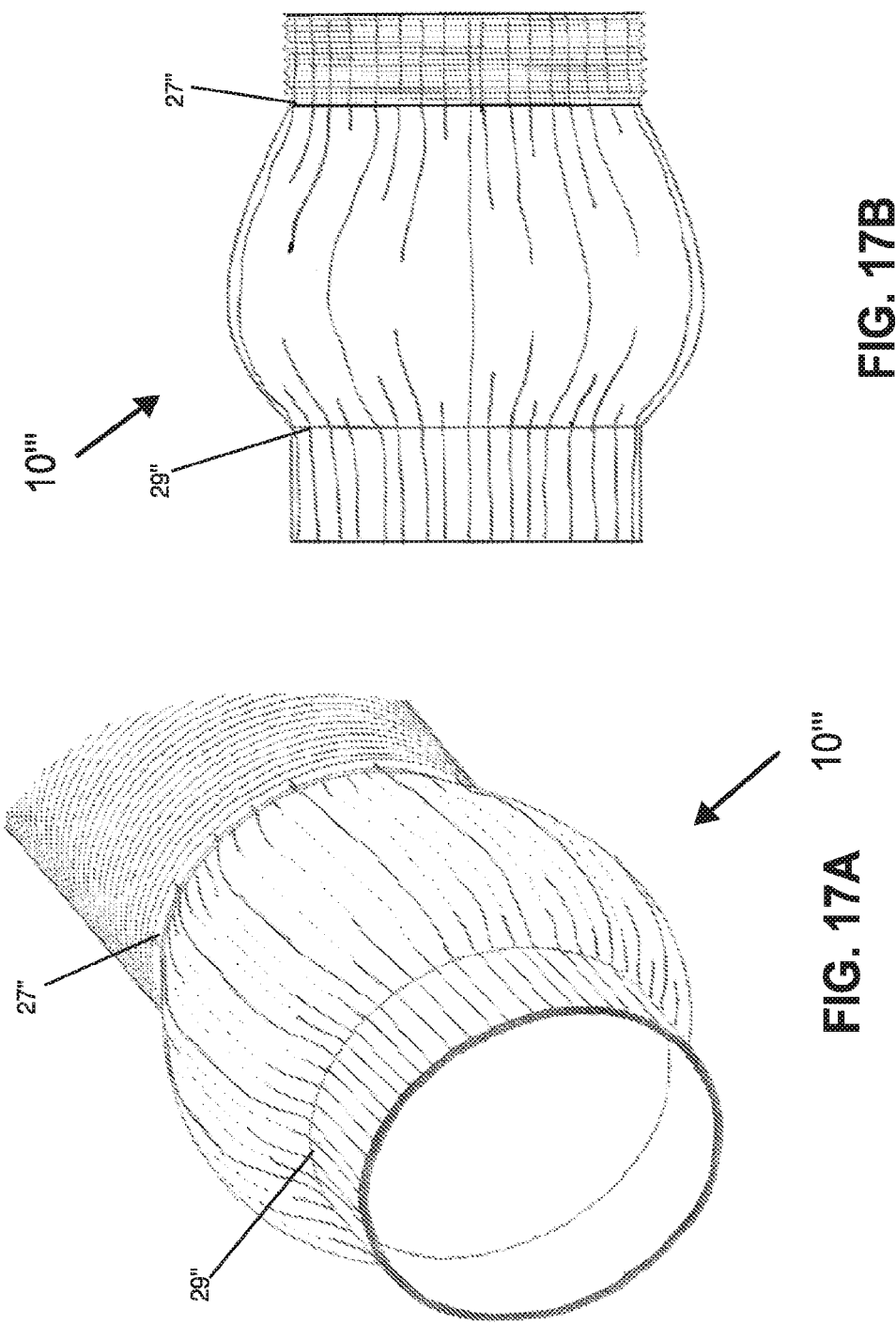

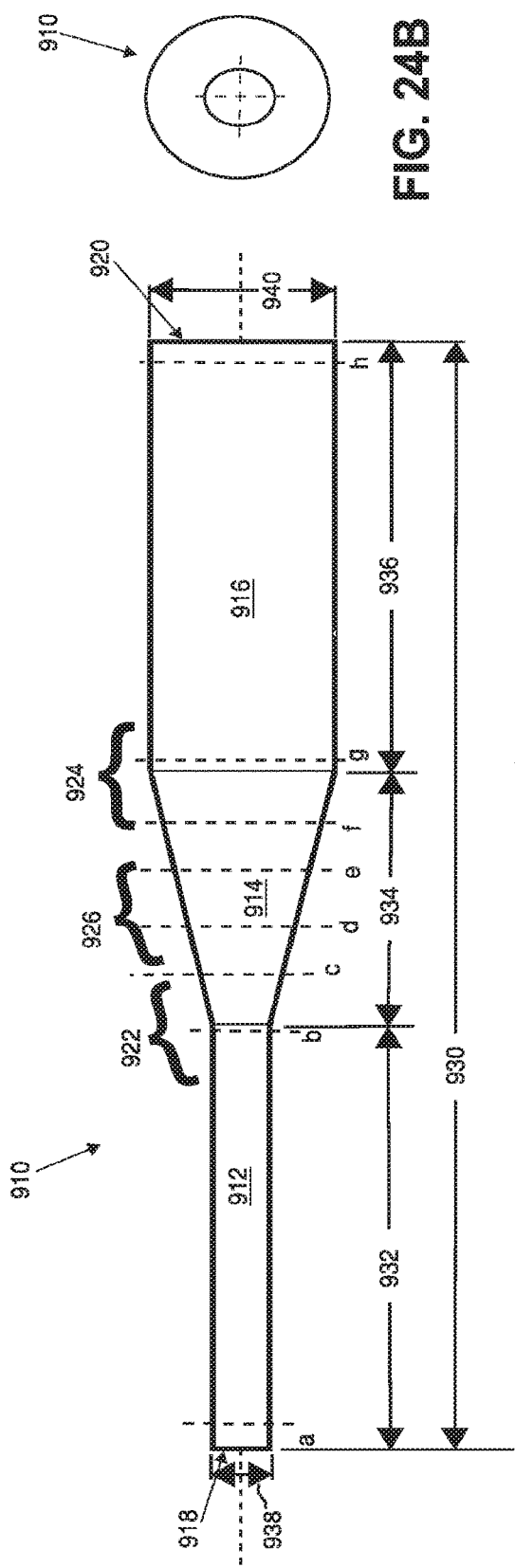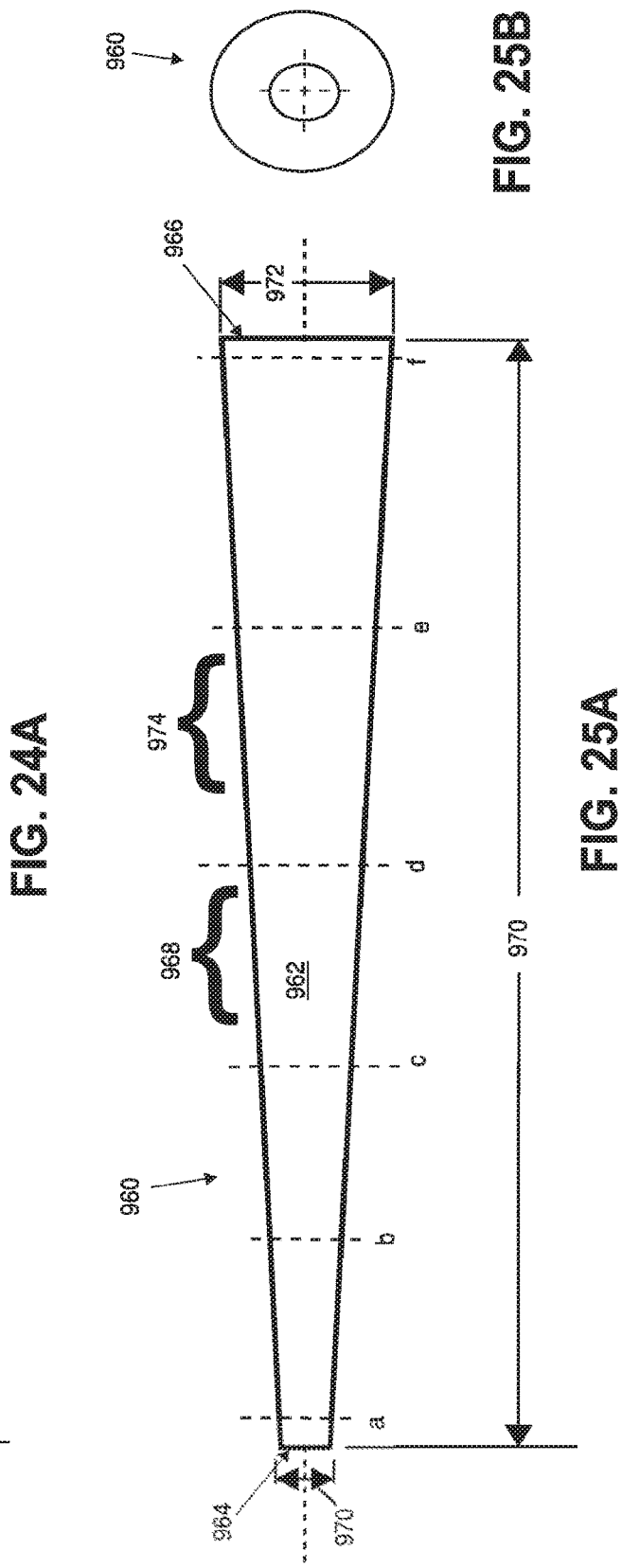

FIG. 26

| Reference Datum | Distance from Proximal End (centimeters) | Total Number of Warp Yarns | Average Base Layer Warp Yarn Density/Spacing [yarns per inch (per cm)] +/- tolerance* | Average Total Warp Yarn Density/Spacing [yarns per inch (per cm)] +/- tolerance* | Average Interior Velour Layer Warp Yarn Density/Spacing [yarns per inch (per cm)] +/- tolerance* | Average Exterior Velour Layer Warp Yarn Density/Spacing [yarns per inch (per cm)] +/- tolerance* | Average Diameter (millimeters) |
|---|---|---|---|---|---|---|---|
| a | 1 | 890 | 200 (79) | 600 (236) | 200 (79) | 200 (79) | 12 |
| b | 10 | 890 | 200 (79) | 600 (236) | 200 (79) | 200 (79) | 12 |
| c | 11 | 890 | 200 (79) | 428 (169) | 114 (45) | 114 (45) | 17 |
| d | 12 | 890 | 200 (79) | 333 (131) | 67 (26) | 67 (26) | 22 |
| e | 13 | 890 | 200 (79) | 273 (107) | 36 (14) | 36 (14) | 27 |
| f | 14 | 890 | 200 (79) | 231 (91) | 15 (6) | 15 (6) | 32 |
| g | 15 | 890 | 200 (79) | 200 (79) | 0 | 0 | 36 |
| h | 24 | 890 | 200 (79) | 200 (79) | 0 | 0 | 36 |

* the tolerance can be within 30% of the average, 20% of the average, 10% of the average, and preferably 5% of the average

| Reference Datum | Distance from Proximal End (centimeters) | Total Number of Warp Yarns | Average Base Layer Warp Yarn Density/Spacing [yarns per inch (per cm)] +/- tolerance* | Average Total Warp Yarn Density/Spacing [yarns per inch (per cm)] +/- tolerance* | Average Interior Velour Layer Warp Yarn Density/Spacing [yarns per inch (per cm)] +/- tolerance* | Average Exterior Velour Layer Warp Yarn Density/Spacing [yarns per inch (per cm)] +/- tolerance* | Average Diameter (millimeters) |
|---|---|---|---|---|---|---|---|
| a | 0.5 | 890 | 200 (79) | 600 (236) | 200 (79) | 200 (79) | 12 |
| b | 5 | 890 | 200 (79) | 428 (169) | 114 (45) | 114 (45) | 17 |
| c | 10 | 890 | 200 (79) | 333 (131) | 67 (26) | 67 (26) | 22 |
| d | 15 | 890 | 200 (79) | 273 (107) | 36 (14) | 36 (14) | 27 |
| e | 20 | 890 | 200 (79) | 231 (91) | 15 (6) | 15 (6) | 32 |
| f | 24.5 | 890 | 200 (79) | 200 (79) | 0 | 0 | 36 |

* the tolerance can be within 30% of the average, 20% of the average, 10% of the average, and preferably 5% of the average

961

WOVEN PROSTHESIS AND METHOD FOR MANUFACTURING THE SAME

CROSS-REFERENCE TO RELATED APPLICATIONS

This application is a continuation of U.S. patent application Ser. No. 16/013,778, filed on Jun. 20, 2018, which is a continuation of U.S. patent application Ser. No. 15/221,801, filed on Jul. 28, 2016 (now U.S. Pat. No. 10,010,401), which is a continuation of U.S. patent application Ser. No. 13/997,095 (now U.S. Pat. No. 9,402,753), which has a 371(c) date of Sep. 9, 2013 and is a nationalization of International Patent Application No. PCT/US2011/067002, filed on Dec. 22, 2011 pursuant to 35 USC § 371, which in turn is a continuation of U.S. patent application Ser. No. 12/978,382, filed on Dec. 23, 2010 (now U.S. Pat. No. 8,696,741). Each of these patent applications (U.S. patent application Ser. No. 16/013,778, U.S. patent application Ser. No. 15/221,801, U.S. patent application Ser. No. 13/997,095, International Patent Application No. PCT/US2011/067002, and U.S. patent application Ser. No. 12/978,382) is expressly incorporated herein by reference in its entirety.

STATEMENT REGARDING FEDERALLY SPONSORED RESEARCH OR DEVELOPMENT

Not applicable.

BACKGROUND OF THE INVENTION

Field of the Invention

The present invention relates to an implantable woven prosthesis and a method for manufacturing same. In an exemplary embodiment, the prosthesis is a tubular graft varying in diameter along its length. The prosthesis may be used, for example, by vascular or cardiovascular surgeons, for repairing portions of the cardiovascular system, including but not limited to all or portions of the ascending aorta, and aortic root. In an exemplary embodiment, the present invention may also applicable to valve sparing and Bentall-type procedures.

Description of Related Art

Tubular woven fabrics have been used for soft-tissue implantable prostheses to replace or repair damaged or diseased lumens in the body. Within the field of cardiothoracic surgery, for example, endoprostheses are used in the vascular system to prevent blood flow and pressure from rupturing a weakened or otherwise damaged section of the vessel. Such endoluminal conduits may be affixed in a specified location in the vessel by means of stents, hooks, sutures, or other mechanisms serving to secure the devices in place. Endoluminal tubular devices or conduits can also be used in other lumens in the body, such as in the esophagus and colon areas.

One area of specialty, replacement or repair of the aortic valve and/or the ascending aorta, in particular the sinuses of Valsalva, involves specialized and time consuming surgical procedures. These procedures have traditionally been performed with straight woven grafts. Although the procedures can be executed with a straight graft prosthesis, there is an increasing perception within the surgical community that vascular grafts incorporating bulges or bulbous portions to mimic the natural shape and profile of the human vasculature may be beneficial. Attempts to fabricate such grafts by others typically have caused problems in one or both of the areas of fabrication, surgical utility, and/or post-operative patency.

For example, some fabrication attempts have involved post-weaving processing such as stitching, suturing, or the seaming of cut sections of corrugated fabrics together in a manner that results in a graft comprising a corrugated expandable middle section. Such a graft requires additional and costly manufacturing steps. Furthermore, the resulting graft can compromise surgical utility and ease of use for the surgeon, since a sufficiently flat and smooth surface is not provided for anastomosis to occur on a bulbous portion. Such deficiencies complicate anastomosis procedures.

Additionally, the "seams" or "junctions" where the multiple components are brought together create localized portions of graft rigidity, strength, and change in porosity not found in other portions of the graft. The resulting non-uniform nature of the underlying graft forces the surgeon to consider orientation of the graft prior to and during implantation and/or anastomosis. This extra precaution required of the surgeon may distract him or her from other aspects of the surgery.

Furthermore, in vivo arterial pressure applied to grafts with corrugated bulbous sections may result in expanded shapes and dimensions that are drastically different when compared to the unpressurized state of such prosthesis commonly occurring during surgery. With such prostheses, the surgeon will therefore not be able to predict the in vivo performance of the prosthesis in terms of the clearance or engagement of valve leaflets with the inner sidewall of the prosthesis. Therefore, the surgeon may not fully appreciate how such a graft will function in vivo, and may not have any predictions as to long-term surgical success of the prosthetic thereby potentially jeopardizing the intended efficacy of the surgical procedure.

Other examples of fabricating prostheses for addressing problems relating to the ascending aorta and sinuses of Valsalva attempt to utilize shrinking characteristics of yarns in a controlled manner such that smaller diameter portions of a graft are created through the shrinking of weft yarns. While tapers may be able to be formed through such a procedure, concerns relating to suture retention strength as well as non-uniform porosity and yarn spacing of the fabric structure can cause problems for surgeons and/or long term durability of the prosthesis, when used for repairing portions of the ascending aorta. Additionally, the fabricator of such prostheses will be limited through the shrink coefficients of the yarns to design geometries of sufficient taper required for mimicking the sinuses of Valsalva.

SUMMARY OF THE INVENTION

An implantable prosthesis according to an example embodiment of the present invention comprises a woven base comprising base warp yarns interwoven with weft yarn passes, the woven base at least partially forming smaller and larger diameter portions of the prosthesis and one or more velour yarns forming part of both the smaller and larger diameter portions. In at least a portion of the larger diameter portion at least one of the one or more velour yarns incorporated into the woven base and exhibiting a weave pattern consistent with the woven base.

According to an example embodiment, within the smaller diameter portion, the at least one of the one or more velour yarns is not incorporated into the woven base and does not exhibit a weave pattern consistent with the woven base.

According to an example embodiment, a spacing between the base warp yarns is maintained approximately the same in the smaller and larger diameter portions without adding additional warp yarns to the larger diameter portion beyond that in the smaller diameter portion.

According to an example embodiment, an increase in diameter of the prosthesis going from the smaller diameter portion to the larger diameter is effected by increasing spacing between the base warp yarns during weaving of the prosthesis.

According to an example embodiment, the spacing between the base warp yarns in the larger diameter portion is made smaller without reducing a diameter of the larger diameter portion by at least one of the one or more velour yarns incorporated into the woven base of the larger diameter portion.

According to an example embodiment, the prosthesis is a generally tubular graft and the larger diameter portion lies within a portion of the graft varying in diameter along a longitudinal axis of the graft and the smaller diameter portion lies within a portion of the graft having a generally uniform diameter.

According to an example embodiment, the prosthesis is a generally tubular graft and the larger and smaller diameter portions lie within a portion of the prosthesis in diameter along a longitudinal axis of the graft.

According to an example embodiment, in at least a portion of the smaller diameter portion the one or more velour yarns exhibit a float that is entirely absent or smaller in the larger diameter portion.

According to an example embodiment, a spacing between the base warp yarns in the smaller diameter portion is within 30% of the size of the spacing in the larger diameter portion.

According to an example embodiment, a spacing between the base warp yarns in the smaller diameter portion is within 15% of the size of the spacing in the larger diameter portion.

According to an example embodiment, a spacing between the base warp yarns in the smaller diameter portion is within 10% of the size of the spacing in the larger diameter portion.

According to an example embodiment, the prosthesis comprises a quantity of the base warp yarns and velour yarns is the same in the larger diameter portion as the smaller diameter portion, and wherein the base warp yarns and the velour warp yarns are continuously woven between the smaller diameter portion and the larger diameter portion.

According to an example embodiment, the prosthesis comprises a secondary woven layer disposed over at least one of the smaller and larger diameter portions, and a portion of a yarn forming the secondary layer is incorporated into the base layer of the larger portion.

An implantable prosthesis according to an example embodiment of the present invention comprises, (i) a woven structure comprising warp yarns interwoven with weft passes, all or a portion of the warp yarns together with the weft passes form a woven base of the woven structure, (ii) a first portion of the woven structure is woven with a first set of the warp yarns, a first subset of the first set of the warp yarns interwoven with the weft passes forms the woven base in the first portion, two of the warp yarns in the first subset in the first portion are spaced apart from each other a first distance along a surface of the prosthesis, the first distance is greater than any spacing between any other pair of warp yarns in the first subset in the first portion along the surface of the prosthesis, (iii) a second portion of the woven structure is woven with the first set of the warp yarns, a second subset of the first set of the warp yarns interwoven with the weft passes forms the woven base in the second portion, two of the warp yarns in the first subset in the second portion are spaced apart from each other a second distance along the surface of the prosthesis, the second distance is greater than any spacing between any other pair of warp yarns in the first subset in the second portion along the surface of the prosthesis. The second distance is greater than the first distance, and the number of warp yarns in the first subset is smaller than the number of warp yarns in the second subset.

According to an example embodiment the portion of the warp yarns interwoven with the weft passes and disposed in the woven base are arranged in a base weave pattern, and another portion of the warp yarns not disposed in the woven base are velour warp yarns.

According to an example embodiment the prosthesis is a generally tubular graft, the first portion having a first diameter along a longitudinal axis of the graft, the second portion having a second diameter along the longitudinal axis larger than the first diameter.

According to an example embodiment the first portion of warp yarns not in the first subset forming the woven base exhibit a float that is entirely absent or smaller in the second portion.

According to an example embodiment, the prosthesis has a first end and a second end, and essentially all the warp yarns are continuously woven between the first and second ends.

According to an example embodiment the prosthesis comprises a secondary woven structure disposed over at least one of the first and second portions, wherein a portion of a yarn forming the secondary woven structure is incorporated into the woven base of the secondary portion.

An example method for making a prosthesis according to the present invention comprises the steps of, (i) weaving a woven base from a set of warp yarns and at least one weft yarn pass the set of warp yarns comprises warp yarns woven as base warp yarns and warp yarns woven as non-base warp yarns, wherein the base warp yarns and weft yarn passes are woven into a base weave pattern, and the non-base warp yarns are woven with at least one weft yarn pass when not woven into a base weave pattern, (ii) incorporating into the woven base one or more of the non-base warp yarns, wherein the one or more non-base warp yarns assume a weave pattern consistent with all or portions of the base weave pattern.

According to an example embodiment the non-base warp yarns are velour yarns.

According to an example embodiment the woven base is configured to establish a smaller and larger diameter portion, and the larger diameter portion is capable of achieving a larger diameter than the smaller diameter portion. The larger diameter of the larger diameter portion is achieved by the step of incorporating into the woven base one or more velour yarns.

An example method for making the graft may further include the step of incorporating into the woven base one or more velour yarns exclusively utilizes velour yarns utilized as velour prior to being incorporated into the base weave pattern.

According to an example embodiment the larger diameter portion has a base warp density within a tolerance of 30% of a base warp density for the smaller diameter portion.

According to an example embodiment the larger diameter portion has a base warp density within a tolerance of 15% of a base warp density for the smaller diameter portion.

According to an example embodiment the larger diameter portion has a base warp density within a tolerance of 10% of a base warp density for the smaller diameter portion.

According to an example embodiment a variable reed is moved during the weaving step to provide for a varied diameter profile of the medical prosthesis.

An example method for making a prosthesis according to the present invention comprises the step of weaving a woven base comprising base warp yarns interwoven with weft yarn passes, the base at least partially forming smaller and larger diameter portions, and one or more velour yarns forming part of both the smaller and larger diameter portions. The example method for making the prosthesis may further comprise weaving in at least a portion of the larger diameter portion at least one of the one or more velour yarns into the woven base to exhibit a weave pattern consistent with the woven base.

According to an example embodiment the at least one of the one or more velour yarns woven into the woven base of the larger diameter portion and exhibiting a weave pattern consistent with the woven base is not woven into the base of the smaller diameter portion.

An example method for making a prosthesis according to the present invention comprises the steps of, (i) weaving a variable diameter graft having a velour layer on at least a portion of the graft, comprising the step of changing a weave pattern of a warp yarn used to form the velour layer in a smaller diameter portion of the graft such that said warp yarn takes on a weave pattern and forms part of a base layer of a larger diameter portion of the graft.

An example method for making the prosthesis may further include the step of changing the weave pattern of the warp yarn as it transitions from the larger diameter portion to a second smaller diameter portion so as to form a velour layer on at least a portion of the second smaller diameter portion which is smaller in diameter than the larger diameter portion.

An example method for making the prosthesis may further include the step of shifting at least a pair of adjacent warp yarns used to form a base layer of the smaller diameter portion so as to increase a spacing between the adjacent warp yarn in the larger diameter portion.

According to an example embodiment a spacing between base warp yarns used to form the smaller diameter portion is within 30% of the size of a corresponding spacing between the same base warp yarns in the larger diameter portion.

According to an example embodiment a spacing between base warp yarns used to form the smaller diameter portion is within 15% of the size of a corresponding spacing between the same base warp yarns in the larger diameter portion.

An example method for making a prosthesis according to the present invention comprises the steps of, (i) forming a first portion of the prosthesis by interweaving base warp yarns, velour warp yarns, and one or more weft yarn passes, (ii) shifting at least a pair of adjacent base warp yarns so as to increase or decrease a spacing between them, and (iii) forming a base layer of a second portion of the prosthesis by weaving the one or more weft yarn passes with the at least a pair of shifted base warp yarns together with one or more of the velour warp yarns.

According to an example embodiment wherein the velour warp yarn exhibits a float in the first portion and no float or less of a float in the second portion.

According to an example embodiment, wherein the shifting is accomplished using a warp yarn guide device.

According to an example embodiment, the warp yarns pass through gaps in the warp yarn guide device and the spaces are spaced apart a distance greater than the spacing between the warp yarns in the first portion of the prosthesis.

According to an example embodiment, wherein the medical prosthesis is a generally tubular graft and the second portion of the graft has a larger diameter than the first portion of the graft.

According to an example embodiment, the shifting is incrementally increased or decreased along a longitudinal axis of the graft so as to effect a change in diameter of the prosthesis.

According to an example embodiment, wherein a spacing between the base warp yarns in the first portion is within 30% of the size of a corresponding spacing between the same base warp yarns in the second portion.

An example method for making the graft may further include the step of using at least one of the base warp yarns from the first portion in the second portion as a velour warp yarn and not as part of the base layer of the second portion.

According to an example embodiment, a quantity of the base warp yarns and velour warp yarns is the same for both the first portion and the second portion.

According to an example embodiment a quantity of the base warp yarns and velour warp yarns is consistent throughout the entire medical prosthesis.

An example method for weaving a prosthesis according to the present invention comprises the steps of, (i) weaving a woven base comprising base warp yarns interwoven with weft yarn passes, the base at least partially forming smaller and larger diameter portions of the prosthesis, one or more velour yarns forming part of both the smaller and larger diameter portions, and (ii) incorporating in at least a portion of the larger diameter portion at least one of the one or more velour yarns into the woven base so as to exhibit a weave pattern consistent with the woven base. According to an example embodiment, incorporating in step (ii) may not be in the smaller diameter portion.

An example method for weaving the prosthesis may further include the step of shifting at least a pair of adjacent warp yarns used to form a base layer of the smaller diameter portion so as to increase a spacing between said adjacent warp yarns in the larger diameter portion.

An example method for making an implantable medical prosthesis according to the present invention and comprising a woven structure comprising warp yarns interwoven with weft passes, all or a portion of the warp yarns together with the weft passes form a woven base of the woven structure, comprises the steps of, (i) weaving a first portion of the woven structure with a first set of the warp yarns, a first subset of the first set of the warp yarns interwoven with the weft passes forms the woven base in the first portion, two of the warp yarns in the first set in the first portion are spaced apart from each other a first distance along a surface of the prosthesis, the first distance is greater than any spacing between any other pair of warp yarns in the first set in the first portion along the surface of the prosthesis, and (ii) weaving a second portion of the woven structure with the first set of the warp yarns, a second subset of the first set of the warp yarns interwoven with the weft passes forms the woven base in the second portion, two of the warp yarns in the first set in the second portion are spaced apart from each other a second distance along the surface of the prosthesis, the second distance is greater than any spacing between any other pair of warp yarns in the first set in the second portion along the surface of the prosthesis.

An implantable prosthesis according to an example embodiment of the present invention comprises (i) a woven base comprising base warp yarns interwoven with weft yarn passes, the base at least partially forming smaller and larger diameter portions of the prosthesis, and (ii) one or more additional warp yarns forming part of both the smaller and larger diameter portions. In at least a portion of the larger diameter portion but not the smaller diameter portion at least one of the one or more additional warp yarns incorporated into the woven base and exhibiting a weave pattern consistent with the woven base.

An implantable prosthesis according to an example embodiment of the present invention comprises a prosthesis comprising a woven base, the base forming all or part of the sidewall of a proximal tubular portion, a larger diameter portion, and a distal tubular portion, the larger diameter portion comprises a maximum diameter, the maximum diameter is 4 or more millimeters larger than a measured diameter within the proximal tubular portion, the larger diameter portion has a length between seventy five percent and one hundred fifty percent of the measured diameter within the proximal tubular portion, the proximal tubular portion and the larger diameter portion have a substantially uniform yarn to yarn spacing within the woven base for warp yarns woven with weft passes within the woven base.

According to an example embodiment the weft passes are woven with the same yarn material and shrinkage attributes throughout the proximal tubular portion, the larger diameter portion, and the distal tubular portion. The shrinkage attributes include coefficients of shrinkage.

According to an example embodiment the weft passes are woven with the same weft yarn throughout the proximal tubular portion, the larger diameter portion, and the distal tubular portion.

According to an example embodiment the larger diameter portion is seamlessly woven with the proximal tubular portion and the distal tubular portion.

According to an example embodiment the same quantity of warp yarns are used to form the proximal tubular portion, the larger diameter portion, and the distal tubular portion.

According to an example embodiment the larger diameter portion is configured to be dimensionally stable under pressurized conditions of 120 millimeters of Mercury.

According to an example embodiment the larger diameter portion is configured to maintain its diameter under fluidic pressurized conditions of 120 millimeters of Mercury.

According to an example embodiment the woven base at the maximum diameter of the larger diameter portion is free of at least one of corrugations, pleats, and crimps.

According to an example embodiment the larger diameter portion is dimensionally stable under pressurized conditions of 120 millimeters of Mercury.

According to an example embodiment, the prosthesis has at least one diameter transition reference indicator.

According to an example embodiment, the diameter transition reference indicator is comprised of weft yarn passes of a different color than other portions of the prosthesis.

According to an example embodiment, the diameter transition reference indicator is formed from one or more weft yarn passes having a color distinguishable from the remaining portion of the prosthesis.

An example method for making an implantable medical prosthesis of the present invention comprises the step of weaving a tubular prosthesis with at least one weft yarn and a plurality of warp yarns, all or a portion of the warp yarns are woven as base warp yarns, velour warp yarns, or both velour and base warp yarns, and wherein the weaving occurs in a longitudinal direction from a smaller diameter portion to a larger diameter portion while maintaining within a predetermined range an average base warp yarn density while decreasing a velour warp yarn density.

According to an example embodiment, a quantity of warp yarns is maintained constant during the step of weaving.

According to an example embodiment, during the step of weaving, the total warp yarn density decreases.

According to an example embodiment, the predetermined range is within a range of plus or minus 30% of an average base warp yarn density throughout the prosthesis, preferably 20% of an average base warp yarn density throughout the prosthesis, and more preferably 10% of an average base warp yarn density throughout the prosthesis, and most preferably 5% of an average base warp yarn density throughout the prosthesis.

BRIEF DESCRIPTION OF THE DRAWINGS

FIG. 8 is an elevation view of a vascular graft according to an example embodiment of the present invention.

FIG. 17A is a perspective view of a graft according to an example embodiment of the present invention.

FIG. 17B is an elevation view of the graft of FIG. 17A.

FIG. 20 is an elevation view of a graft according to an example embodiment of the present invention.

FIG. 21 is an elevation view of a graft according to an example embodiment of the present invention.

FIG. 22 is an elevation view of a graft according to an example embodiment of the present invention.

FIG. 23 is an elevation view of a graft according to an example embodiment of the present invention.

FIG. 24A is an elevation view of a vascular graft according to an example embodiment of the present invention.

FIG. 24B is an end view of the embodiment of FIG. 24A.

FIG. 25A is an elevation view of a vascular graft according to an example embodiment of the present invention.

FIG. 25B is an end view of the embodiment of FIG. 25A.

FIG. 26 is a table of potential parameters according to an example embodiment of the present invention.

FIG. 27 is a table of potential parameters according to another example embodiment of the present invention.

DETAILED DESCRIPTION OF THE PRESENT INVENTION

Figure 1:
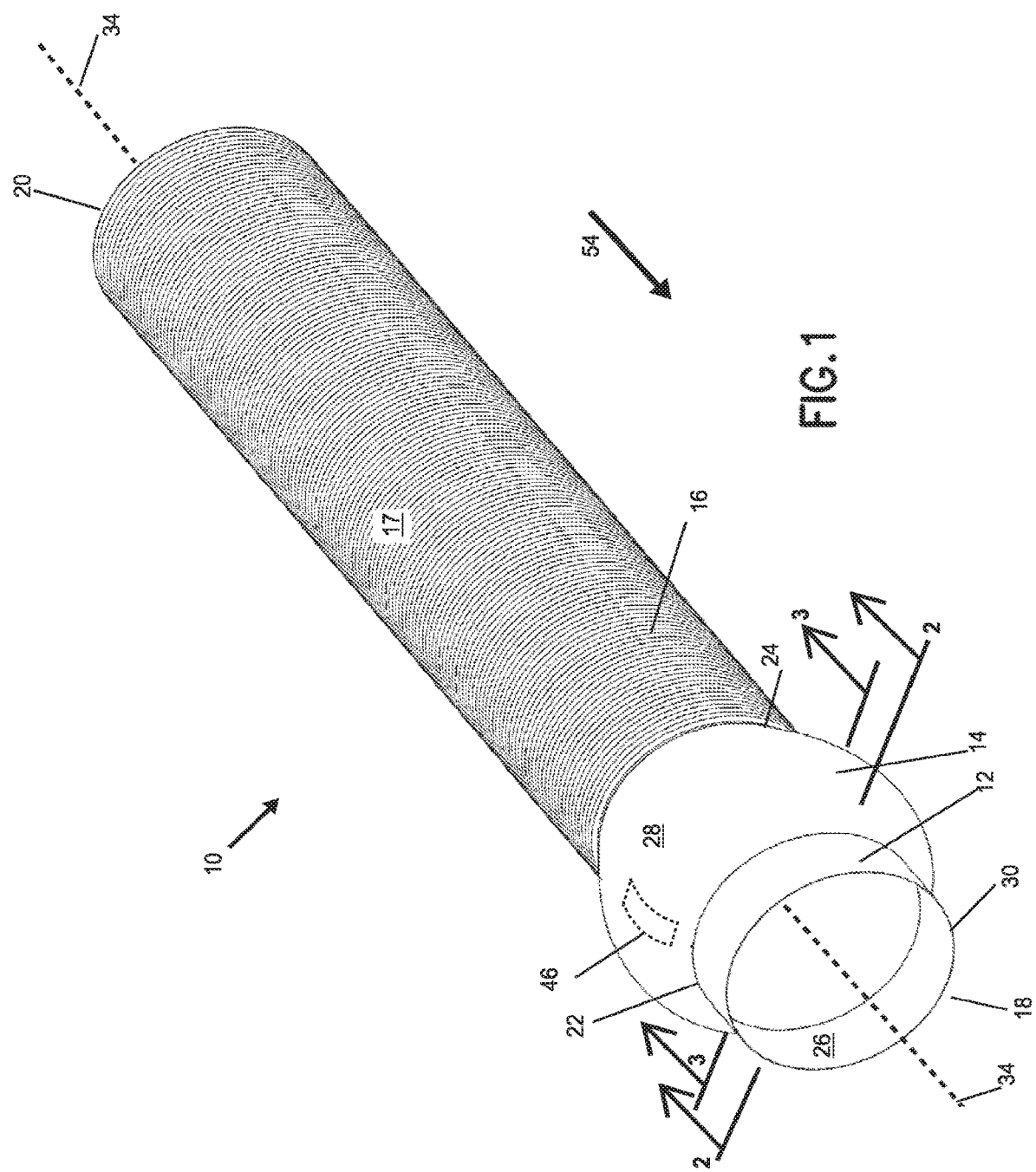
FIG. 1 is perspective view of a vascular graft according to an example embodiment of the present invention.

For purposes of the description hereinafter, the words "upper", "lower", "right", "left", "vertical", "horizontal", "top", "bottom", "lateral", "longitudinal", "axial", and like terms, if used, shall relate to the invention, as it is oriented in the drawing figures. When appropriate, the term "proximal" shall refer to the relative location of an aspect of a prosthesis, directed towards a heart such as a human heart, and the term distal shall refer to a relative location of an aspect of prosthesis in a direction away from a heart. It is to be understood that the invention may assume many alternative variations and embodiments except where expressly specified to the contrary. It is also to be understood that the specific devices and embodiments illustrated in the accompanying drawings and described herein are simply example embodiments of the invention.

FIG. 1 illustrates a varied-diameter prosthesis 10 according to an example embodiment of the present invention configured, for example, as a replacement for the aortic root or ascending aorta. Prosthesis 10 includes a first woven tubular portion 12, a bulbous second woven portion 14, and a third woven tubular portion 16. Prosthesis 10 further comprises a proximal end 18, a distal end 20, and a sidewall 30 disposed therebetween. The sidewall 30 is continuously woven thereby using continuous warp yarns between the ends of the woven structure, such as the proximal 18 and distal end 20, without the need for cutting apart or welding together the warp yarns in between the ends. Other example configurations of the prosthesis 10 are illustrated in FIGS. 8, 16A, 16B, 17A, 17B, 20 to 23, 24A, 24B, 25A, and 25B.

The sidewall 30 of prosthesis 10 shown in FIG. 1 is configured to resist a predetermined level of blood leakage. The leakage rate may be controlled by adjusting the porosity of the sidewall 30 by, for example, adjusting the weave pattern, yarn spacing, yarn denier, and/or yarn tightness. Such attributes of sidewall 30 will provide for a uniform porosity sufficient to provide for tissue ingrowth, yet not cause or promote leakage. The porosity of sidewall 30 can be generally uniform throughout prosthesis 10 before and/or after an optional coating application. Coating applications including collagen or gel coatings may be employed depending on the desired configuration by the fabricator. Desirably, a porosity of sidewall 30 after a coating step may be less than 5 milliliters per centimeter squared per minute at 120 mm Hg. This may be measured using the Wesolowski method.

A variety of weave patterns may be employed. When warp yarns of the present disclosure engage consecutive weft passes, this is commonly known as a plain weave pattern. Additionally, when warp yarns skip, jump, or float over a plurality of weft passes (greater than the skip utilized in the base), these warp yarns are referred as to velour warp yarns and the weave pattern is referred to as a velour weave pattern. A variety of weave patterns may be chosen for both the base as well as portions other than the base, such as warp yarn patterns for those warp yarns not in the base. Examples of non-base warp yarn patterns include velour weave patterns for warp yarns not in the base. Velour weave patterns may include single velour, double velour, and others. Generally, the frequency of interlacing of weft pass is greater for warp yarns when in the base than it is for warp yarns when in a non-base layer such as a velour layer.

Prosthesis 10 is generally elongate, and is woven with warp yarns arranged generally parallel to an axis 34 shown in FIG. 1. First and second tubular portions 12 and 16 are shown as straight tubular portions and are continuously interwoven with the bulbous portion 14 disposed between the tubular portions 12 and 16. The prosthesis 10, 10,' 10," 10,'" 310, 410, 510, 610, 910, and 960 depicted in FIGS. 1, 8, 16A, 16B, 17A, 17B, 20 to 23, 34A, 24B, 25A, and 25B represents just a few examples of the universe of complex contoured vascular prosthetic structures capable of being produced utilizing the techniques of the present invention, and other variations within the scope of the claimed invention are contemplated.

Figure 2:
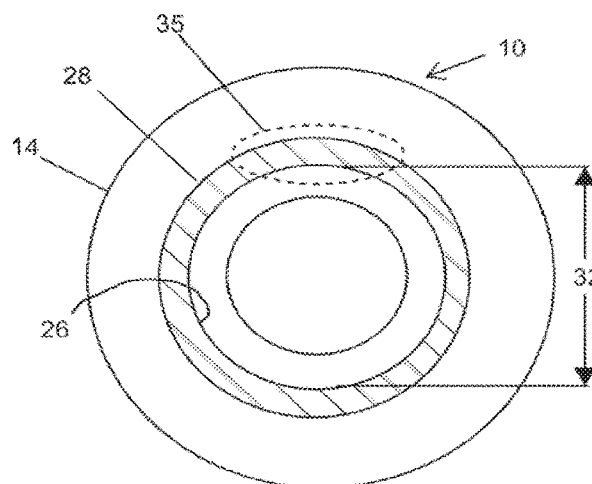
FIG. 2 is a cross sectional view taken along lines 2-2 in FIG. 1.

FIG. 2 illustrates a highly schematic cross section taken about line 2-2 in FIG. 1. The diameter of the prosthesis 10 at line 2-2 is labeled using reference number 32. As discussed further below, the prosthesis 10 as illustrated in FIG. 2 has already undergone processing steps so as to allow it to maintain this substantially self-supporting configuration. Prior to this processing, the prosthesis has a more flattened profile common to greiges.

Figure 3:
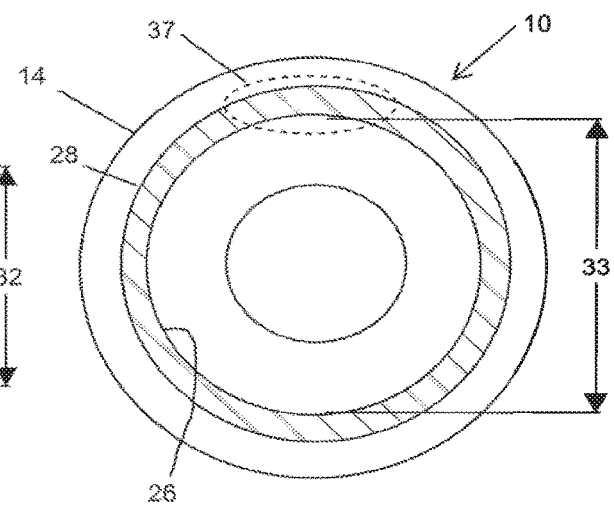
FIG. 3 is a cross sectional view taken along lines 3-3 in FIG. 1.

FIG. 3 illustrates a highly schematic cross section taken about line 3-3 in FIG. 1. The diameter of the prosthesis 10 at line 3-3 is labeled as reference number 33. Line 3-3 intersects prosthesis 10 at a larger diameter than line 2-2, and thus the diameter 33 is larger in magnitude than the diameter 32.

Figure 4A:
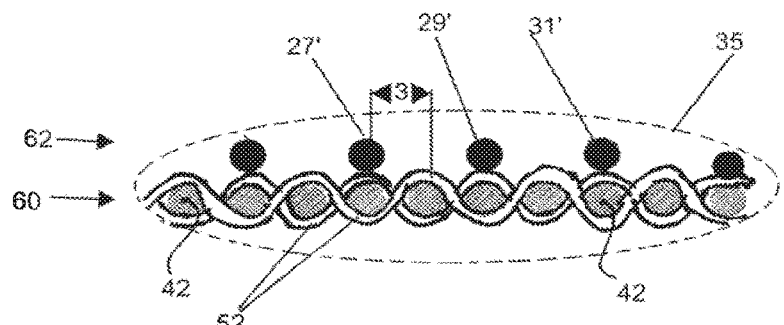
FIG. 4A is a partial sectional view of a portion of the graft of FIG. 2.

FIG. 4A is a magnified view of a circumferential section 35 of prosthesis 10 shown in FIG. 2. Illustrated is a cross section of the sidewall, comprising a total of fifteen warp yarns 40, and two weft passes 52. A first set of warp yarns (fifteen as illustrated) are shown, ten of which are interwoven with a first set of weft passes 52 (two weft yarns as shown), and comprise a first subset of the first set or base layer 60. The term "base" is meant to be interchangeably used with the terms "base layer", "foundation", "ground" or "ground layer." The remaining warp yarns make up a second set of warp yarns, and are positioned outside the base layer 60, in a non-base layer, such as a velour layer 62. This second set comprises among the five non-base warp yarns, yarns 27', 29', and 31'. In this embodiment, the non-base velour layer provides a loose weave (relative to the base layer 60) allowing for tissue ingrowth into the prosthesis 10 during usage as a vascular conduit and, thus, functions as a velour layer.

Figure 4B:
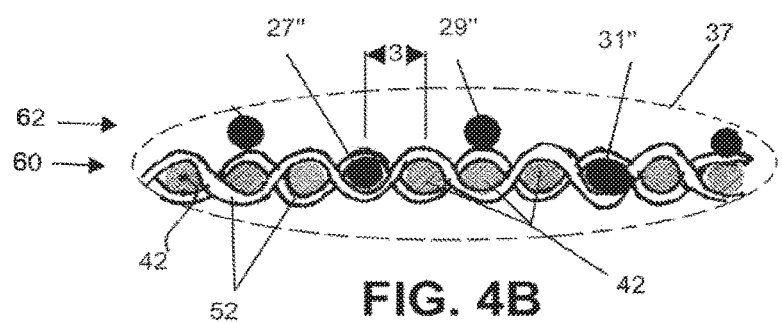
FIG. 4B is a partial sectional view of a portion of the graft in FIG. 3.

Similar to FIG. 4A, FIG. 4B represents a magnified view of a circumferential section 37 of prosthesis 10 shown in FIG. 3 taken over the same arc as section 35. Illustrated is a cross section of the sidewall, including a total of thirteen warp yarns 40, and two weft passes 52. A first set of warp yarns 40 (thirteen as illustrated) are shown, ten of which are interwoven with a first set of weft passes 52 (two weft yarns as shown), and comprise a first subset of the first set or base layer 60. Two warp yarns of the first subset of the first set are warp yarns 27" and 31", which are the same warp yarns 27' and 31' illustrated in FIG. 4A, but now positioned in FIG. 4B as interwoven with weft passes 52 and in the base layer 60. The two warp yarns 27 and 31 have therefore have been shifted from a first position in a non-base layer (velour layer 62) illustrated in FIG. 4A (as warp yarns 27' and 31'), to a base layer 60 illustrated in FIG. 4B (as warp yarns 27" and 31").

Despite the diameter increase between FIG. 2 and FIG. 3, it should be noted that a center-to-center distance or spacing 3 between adjacent warp yarns 40 in both FIGS. 4A and 4B is the same or approximately the same. The expanded diameter in the bulbous portion 14, therefore, does not come at the expense of increased prosthesis porosity in this portion 14, which can cause blood leakage as well as reduce suture integrity during procedures such as anastomosis. Rather, shifting warp yarns 27' and 31' in the non-base layer 62 into the base layer 60 during weaving of the prosthesis 10 allows for an increased diameter in the second woven portion 14 while still maintaining the yarn density, and thus porosity of the prosthesis 10, in this portion 14. Shifting the warp yarns 40 apart, absent any other intervention, necessarily decreases the yarn density of the prosthesis 10 in the bulbous portion 14.

In an exemplary embodiment, rather than shifting both yarns 27' and 31' into the base layer 60, only one of yarns 27' and 31' may be shifted into the base layer. In this case, spacing between adjacent warp yarns will increase compared to that as shown in FIGS. 4A and 4B. This may be desirable to the extent a reduced porosity is desired in the bulbous second portion 14 as compared to, for example, the first woven tubular portion 12, while still maintaining the porosity above a level allowing for blood leakage.

Throughout the present disclosure, including FIGS. 4A and 4B, when the warp yarns are located in a base layer of the prosthesis and have adopted a weave pattern or first weave pattern consistent with the base layer, the warp yarns when in the base layer 60 are referred to generically as base warp yarns. Furthermore, when the warp yarns are not in the base layer 60 and have not adopted the weave pattern of the base layer 60, or have adopted a second weave pattern different from the first weave pattern, the warp yarns may be referred to within the present disclosure as non-base warp yarns, such as, but not limited to velour warp yarns. Some warp yarns may be positioned and/or woven as a base warp yarn throughout all or just a portion of the entire prosthetic structures described herein. Some warp yarns may be positioned and/or woven as a velour warp yarn throughout all or just a portion of the prosthetic structures described herein. Further, some warp yarns may serve as both velour warp yarns and base warp yarns and may transition between the two states by a transition or adjustment in weave pattern or frequency of interlacing.

Figure 5:
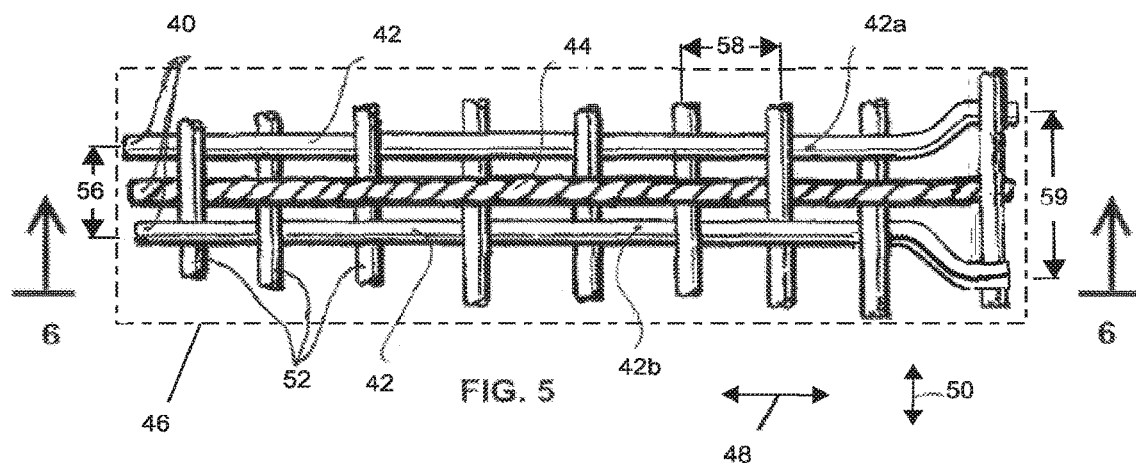
FIG. 5 is a magnified top view of a portion of the graft surface in FIG. 1.

FIG. 5 is a magnified view of a portion 46 (circumscribed in dashed lines for reference only) of an external surface 28 of prosthesis 10 as shown in FIG. 1. Three warp yarns (generally referenced as warp yarns 40) are shown woven with a plurality of weft passes 52. The warp yarns extend in a direction correlating to arrows 48, while the weft passes 52 extend in directions that correlate with arrows 50. Other directions may be employed without departing from the spirit of the invention, and the directions shown are merely illustrative. Arrows 48 are generally consistent with the axis 34 in FIG. 1.

Of the warp yarns 40 illustrated in FIG. 5, two of the warp yarns 40 are base warp yarns 42 throughout the entire figure, and one of the warp yarns 44 exhibits behaviors of both a base warp yarn, such as warp yarns 42, as well as a non-base warp yarn, such as a velour warp yarn. The non-base warp yarn 44 exhibits both a first weave pattern, i.e., a 5/1 velour pattern, and a second weave pattern, i.e., a 1/1 plain weave pattern. In the 5/1 velour pattern, the warp yarn 44 (shown cross hatched for illustrative purposes only) passes under a first weft pass 52 (first to the left in FIG. 5), and floats over five subsequent weft passes 52 before passing under the third to last right most weft pass 52. After passing under the third to last right most weft pass 52, warp yarn 44 transitions to a base warp yarn by adopting a repeating over and under 1/1 plain weave pattern for the remaining weft passes 52.

Consistent with the above, base warp yarns 42a and 42b engage each of the nine subsequent weft passes 52 from left to right. Specifically, base warp yarn 42a is positioned below the first weft pass while base warp yarn 42b is positioned above the first weft pass. This pattern repeats such that all of the nine weft passes shown in FIG. 5 are interwoven with the first and second base warp yarns 42a, 42b.

On the right most side of portion 46, where warp yarn 44 is woven/incorporated into the base 60, and adopts a weave pattern consistent with the base (such as the 1/1 weave pattern shown for base warp yarns 42a, 42b), adjacent base warp yarns 40 are shifted apart from each other in the base layer 60 and accommodate this incorporation. This relative shifting of the base warp yarns 40 in the base layer 60 as illustrated occurs before the transition in weave pattern but may also occur at or after the transition in weave patterns. As detailed below, a warp yarn guide device (FIGS. 13A-13C and 14A-14C), such as a fan-shaped reed, may be used to adjust the spacing between the warp yarns 40. When warp yarn 44 is moved into the base layer 60, warp yarn 44 adopts the same weave pattern as one or both of base warp yarns 42a, 42b. Warp yarn 44, when in the base layer 60, is in-phase with base warp yarn 42a, and out-of-phase with base warp yarn 42b.

First warp yarn spacing 56 designates the space between adjacent base warp yarns 42a, 42b in the base layer 60 when additional warp yarns are not interwoven between the base warp yarns 42a, 42b with a weave pattern consistent with the base warp yarns 42a, 42b. Second warp yarn spacing 59 designates the larger center to center distance between adjacent warp yarns 42a, 42b in the base layer 60 to the right of portion 46 where the yarns 42a, 42b been shifted apart.

Figure 6:
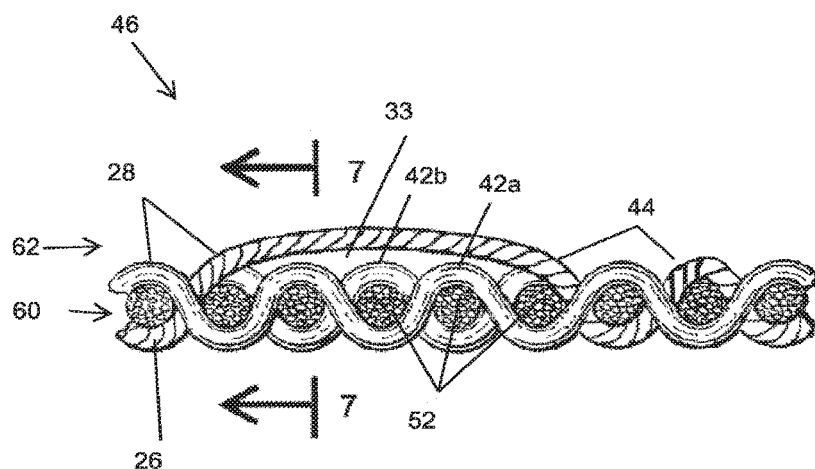
FIG. 6 is a sectional view taken along lines 6-6 in FIG. 5.

FIG. 6 illustrates a side view of portion 46 of external surface 28, taken through lines 6-6 in FIG. 5. FIG. 6 illustrates how warp yarn 44 floats over five weft passes 52 as a velour warp yarn, engage, i.e., pass under, an additional weft pass (the sixth from the left), and change weave patterns to adopt a base weave pattern by floating above and below consecutive weft passes. While FIG. 6 demonstrates a gap or spacing 65 between warp yarn 44 and the base warp yarns 42 when warp yarn 44 is not in the base layer 60, the warp yarn 44 may be woven in a manner such that no space or gap exists. Also, while FIG. 5 illustrates the warp yarn 44 only projecting from surface 28 (an outer surface of the prosthesis 10), the velour warp yarn 44 may be flipped such that it projects only from an inner surface of the prosthesis, or optionally from both the inner and outer surfaces 26, 28. Further, while a float over five weft passes is illustrated other floats may be used as well.

Figure 7:
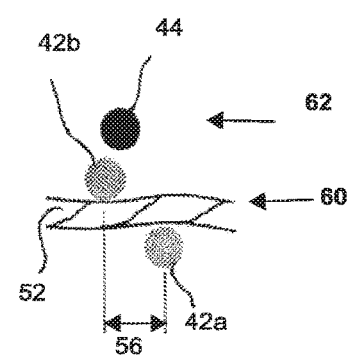
FIG. 7 is a sectional view taken along lines 7-7 in FIG. 6.

FIG. 7 illustrates a cross sectional view taken through lines 7-7 of FIG. 6. First base warp yarn 42a and second base warp yarn 42b are shown to have different elevations, with a weft pass disposed therebetween, but they may also be arranged so as to be at the same elevation. A dashed line is included in FIG. 7 for illustrative purposes to distinguish between the base layer 60 below the dashed line and the non-base layer 62 above the dashed line.

As indicated above, base warp yarns 42a, 42b and the interposed weft passes 52 form the base layer 60 further illustrated in FIG. 7 and lateral distance 56 represents the center-to-center distance between the first and second warp yarns 42a, 42b. This distance 56 (see also FIG. 5) between adjacent warp base warp yarns may be adjusted, e.g., so as to make space for one or more velour warp yarns to be incorporated into the base layer 60 and adopt a weave pattern consistent with the base layer 60. To the extent desirable, e.g., to control porosity, suture retention strength, or permeability to blood of the prosthesis, distance 56 may also be decreased when a base warp yarn moves out of the base layer 60 and adopts a weave pattern consistent with a non-base weave pattern, such as a velour weave pattern.

Warp yarns may be systematically moved from a first position in a non-base layer 62, hence outside of base layer 60 of the woven structure, to a second position within the base layer 60. In the first position, the warp yarns are woven in a manner in which they engage weft passes, and may for example be woven in a velour-type manner, floating over a plurality of weft yarn passes, adopting a non-base 62 weave pattern such as a velour weave pattern. Alternatively, in the first position, the warp yarns may be woven in a layer not in the base, such as in a multi-layered or three dimensional fabric structure, wherein the base comprises one of the layers, and the other layer(s) may comprise the non-base layer 62. In the second position, the warp yarns are woven into the base layer 60, preferably in a manner whereby the warp yarns adopt or take on the weave pattern of the base 60.

When the warp yarns are moved into the base of the woven structure, some or all of the base warp yarns may be moved laterally with respect to each other so that the warp yarn brought into the base has sufficient space to adopt a weave pattern consistent with the base, and also provide for a controlled base warp yarn density (e.g., a consistent warp yarn density). Warp yarn density is typically measured in warp yarns per given unit of length of fabric. For clarity, in the present disclosure, woven yarn density will relate to a given length of the woven structure that can be measured for instance in a generally taut state, i.e., drawn tight sufficient to remove slack. The density is measured as the quantity of yarns per given unit of length.

FIG. 8 illustrates an example embodiment of woven prosthesis 10' of the present invention. Similar to FIG. 1, the prosthesis 10' is illustrated as having a first tubular portion 12', a second bulbous portion 14', and a third portion 16'.The second tubular portion 16, 16' has a crimped surface 17, 17' but may also be non-crimped. The crimped surface 17, 17' can be circularly crimped, helically crimped, or configured with combinations thereof.

Figure 9:
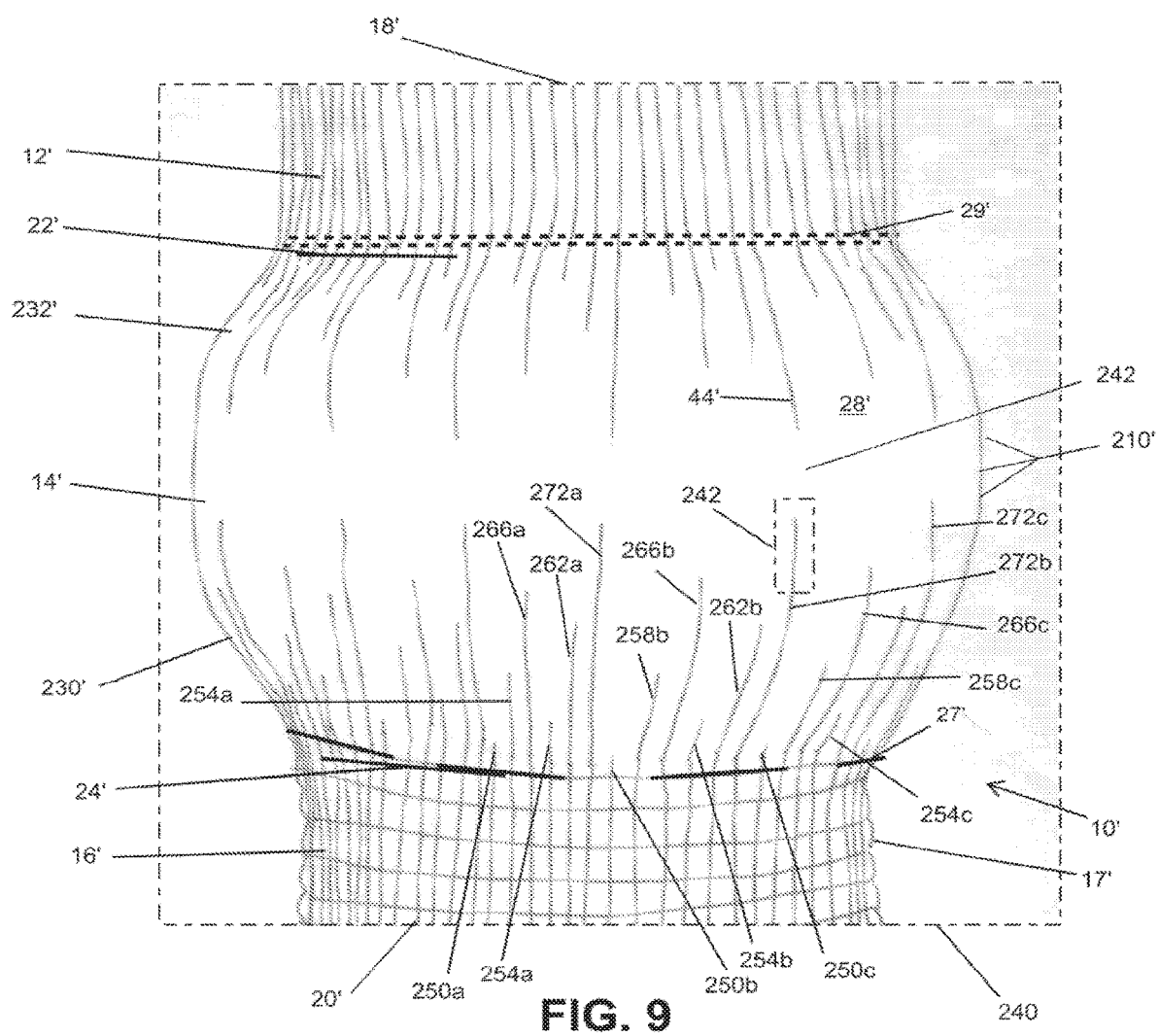
FIG. 9 is a magnified view of a bulbous portion and adjacent portions of the graft of FIG. 8.

FIG. 9 is a magnified view of a portion of the prosthesis 10' of FIG. 8 taken about a dashed line border 240. As can be seen in FIG. 9, circumferentially spaced velour warp yarns 44' are woven into the prosthesis 10' and extend longitudinally along the prosthesis 10'. The circumferential center-to-center spacing of the velour warp yarns 44' is adjustable. Also adjustable is the pattern, sequence, or rate in which the velour warp yarns 44' are longitudinally transitioned into and out of the base layer 60 (FIGS. 12A-12C).

A plurality of groups of velour warp yarns (250, 254, 258, 262, 266, and 270) are shown in FIG. 9. Each group is representative of a plurality of warp yarns that share a characteristic relating to the positioning of the groups of warp yarns. Shown for example in FIG. 9 are a plurality of groups, three of which are illustrated with suffixes a through c for the groups of velour warp yarn 250, 254, 258, 262, 266, and 270. A first group of velour warp yarns 250 is represented by velour warp yarns (or sets of velour warp yarns) 250a, 250b, and 250c. These yarns may be brought into the base and adopt a weave pattern consistent with the base at the same or similar time during the weaving process. Subsequent to velour warps yarns 250a, 250b, and 250c being moved into the base, additional velour warp yarns such as a second group of warp yarns 254 comprised of velour warp yarns 254a, 254b, and 254c may be brought into the base. The process of moving one or more groups of velour warp yarns into the base can intentionally be arranged to correlate to the vertical positioning of a reed 120 and can be used to maintain base warp yarn density, and control the diameter of the prosthesis such as to increase or decrease the diameter. This process as applied to groups of velour warp yarns 250 and 254 can be subsequently adapted to additional groups, such as 258, 262, 266, and 270. This process, therefore, can be used to controllably expand the diameter of the woven prosthesis.

Figure 10:
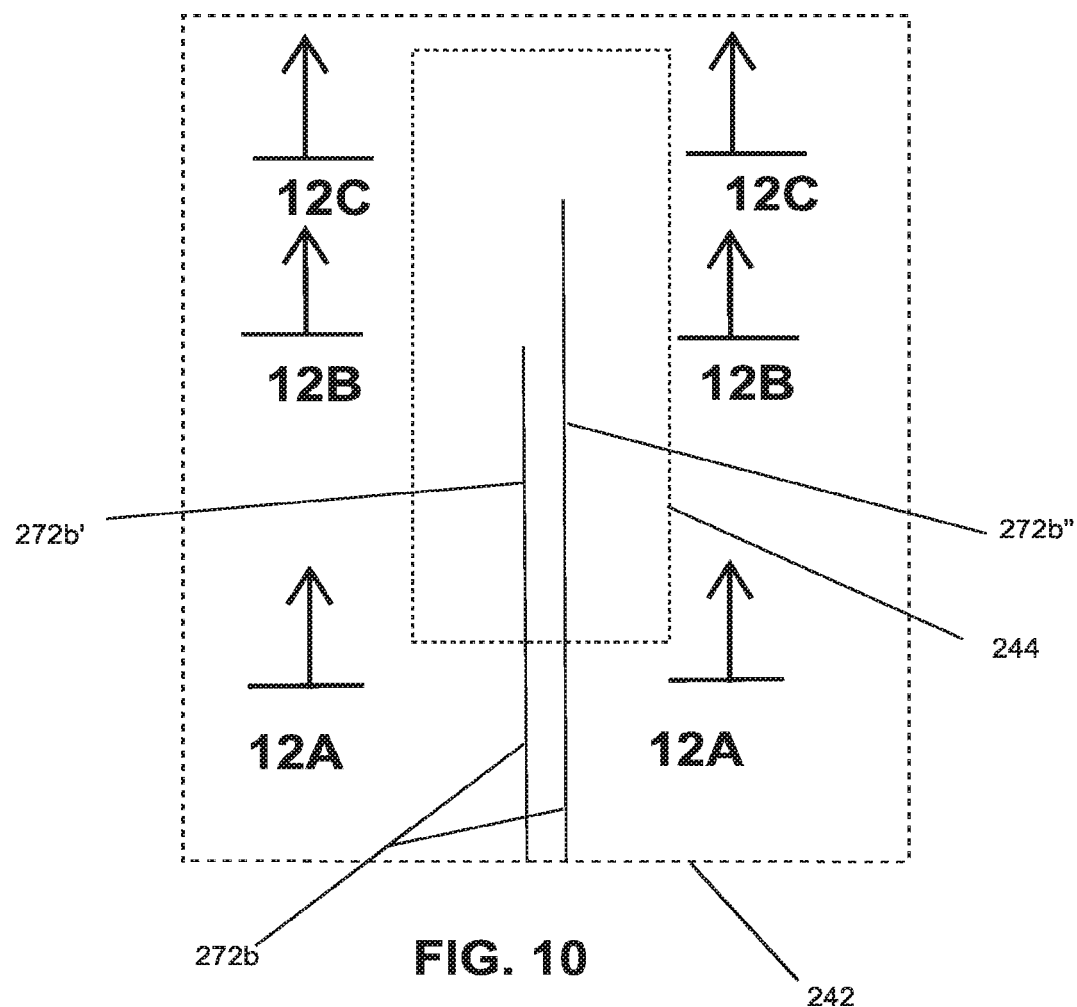
FIG. 10 is a magnified view taken of a portion of the graft as shown in FIG. 8 and FIG. 9.
Figure 11:
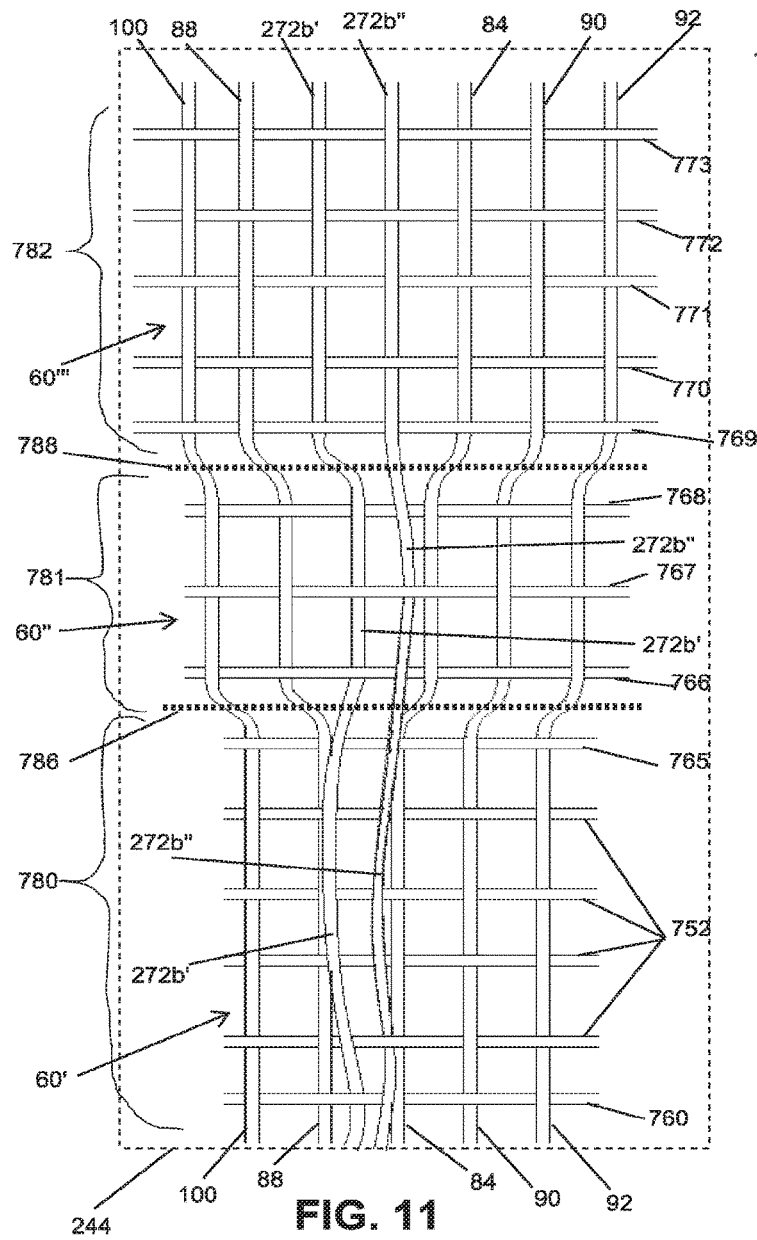
FIG. 11 is a magnified view of a sub-portion of the portion illustrated in FIG. 10.
Figure 13C:
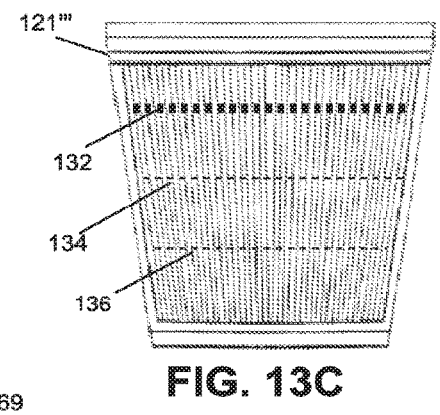
FIG. 13C is an elevation view of a fan-shaped reed in a third position.
Figure 13B:
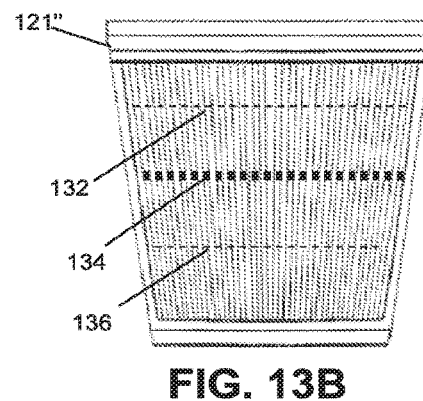
FIG. 13B is an elevation view of a fan-shaped reed in a second position.
Figure 13A:
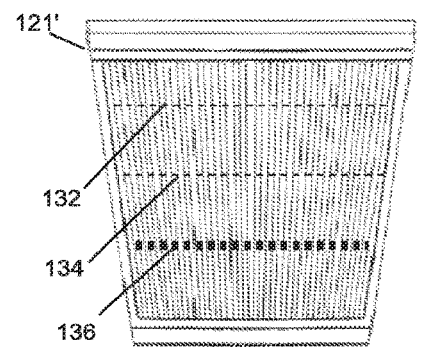
FIG. 13A is an elevation view of a fan-shaped reed in a first position.

FIG. 10 is a magnified view of a portion of the bulbous section 14' shown in FIG. 9 and circumscribed by dashed line border 242 for illustration purposes. The portion circumscribed by dashed border 242 includes one of the many velour warp yarns 44' spaced about and woven into prosthesis 10'. In the magnified view of FIG. 10, it can be seen that the portion circumscribed by border 242 actually may include two velour warp yarns 272b', 272b" that are closely spaced. For added clarity, FIG. 11 is a magnified view of the portion of the prosthesis 10' circumscribed by dashed border 244 in FIG. 10.

Figure 12A:
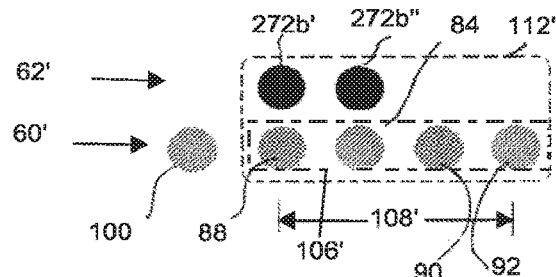
FIG. 12A is a sectional view taken along lines 12A-12A in FIG. 10.
Figure 12B:
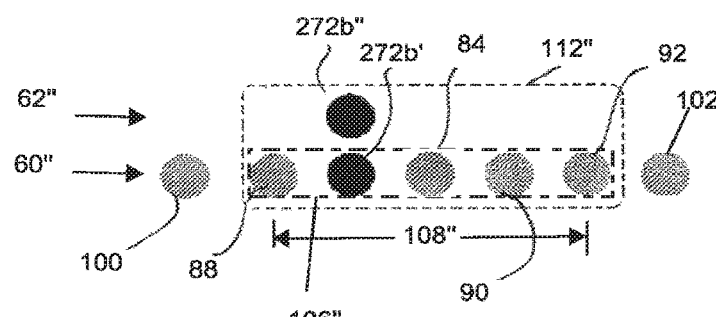
FIG. 12B is a sectional view taken along lines 12B-12B in FIG. 10.
Figure 12C:
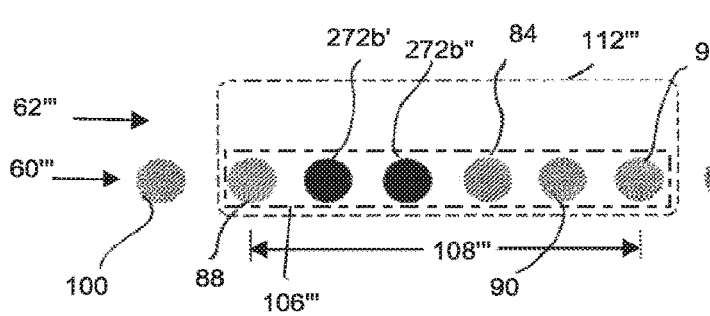
FIG. 12C is a sectional view taken along lines 12C-12C in FIG. 10.

FIGS. 12A, 12B, 12C are sectional views shown in FIG. 10 taken along lines 12A-12A, 12B-12B, and 12C-12C, respectively. For illustrative clarity, the weft yarns are not shown. As the prosthesis 10' is woven, and as further detailed below, velour warp yarns 272b', 272b" are progressively shifted from the velour layer 62', 62", 62"' into the base layer 60', 60", 60"', e.g., so as to maintain a warp yarn density of the base layer 60 while increasing a width 108', 108", 108"' defined by a first set of warp yarns 84, 88, 90, 92. This pattern or technique can be used in a repetitive manner throughout a prosthesis, to thereby produce a large diameter bulbous portion (such as bulbous portions 14, 14' illustrated in FIGS. 1 and 8), as well as manage porosity, warp yarn density, or other properties of a prosthesis. The technique may also be used to construct varied diameter embodiments of other shapes and geometries such as those illustrated in FIGS. 20-23, 24A and 25A.

Shown in FIG. 12A are a first set of warp yarns 112' with six warp yarns in the set, however other quantities are possible. First set of warp yarns 112' has a plurality of base warp yarns 84, 88, 90, 92 in a base 60' thereby defining a first subset 106'. Additionally shown in a non-base layer, such as a velour layer 62', are one or more velour warp yarns 272b', 272b". Flanking or adjacent to each side of the first set of warp yarns within border 112' are additional base warp yarns 100, 102. Two warp yarns within the first subset of warp yarns circumscribed by border 106' are spaced apart from each other a first distance 108', a distance greater than the distance of any other pair of base warp yarns in the first subset circumscribed by border 106'.

Figure 14A:
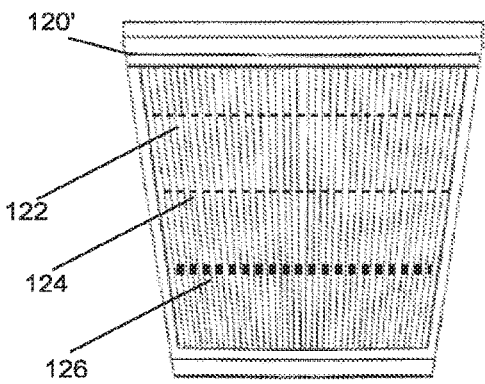
FIG. 14A is an elevation view of a fan-shaped reed in a first position.

Pertaining to the warp yarns of FIG. 12A, a warp yarn guide device, such as a fan-shaped reed 120', may be used to control warp yarn spacing. As shown in FIG. 14A, fan shaped reed 120' has three positions (e.g., 122, 124, and 126) where warp yarns intersect the reed 120' to control spacing during weaving. Correlating to the warp yarns arranged in FIG. 14A, the position of fan shaped reed 120' is used to help achieve the weave pattern of FIG. 12A and is shown to be in a "high" position whereby the reed 120' engages warp yarns at a low location 126. The reed 120' is progressively lowered (or raised depending on its orientation) so as to shift the base warp yarns 84, 88, 90, 92 apart making space for the velour warp yarns 272b', 272b" to be incorporated into the base layer 60', 60", 60"'.

Shown in FIG. 12B is the first set of warp yarns from FIG. 12A with a different arrangement and circumscribed by dashed border 112". The first set of warp yarns in FIG. 12B differs from that of FIG. 12A in that velour warp yarn 272b' has been shifted into the first subset 106" or base layer 60". Therefore, in the first subset 106" of the first set of warp yarns circumscribed by dashed border 112", there are now five base warp yarns instead of four. Reed 120" may be shifted to the middle position to shift the base warp yarns sufficiently to accommodate velour warp yarn 272b' in the base layer 60".

Figure 14B:
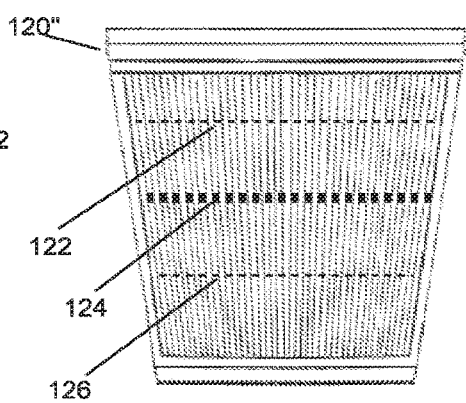
FIG. 14B is an elevation view of a fan-shaped reed in a second position.
Figure 14C:
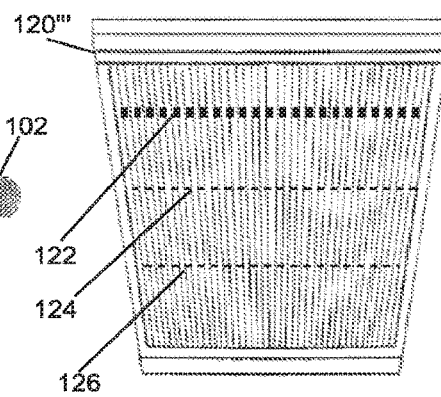
FIG. 14C is an elevation view of a fan-shaped reed in a third position.

Reed 120"' may be shifted even further to the low position illustrated in FIG. 14C so as to allow for velour yarn 272b" to be incorporated in base layer 60"', as illustrated in FIG. 12C. In this state, the base layer 60"' circumscribed by dashed line 106"' holds six base warp yarns.

The distance 108"' shown in FIG. 12C has increased to be greater than distances 108' and 108" shown in FIGS. 12A and 12B, respectively. Even though the distance 108"' has increased, the warp yarn density of the base layer 106"' is maintained relatively consistent with the warp yarn densities of one or both of the arrangements depicted in FIGS. 12A and 12B. Additionally, the velour warp yarn density in terms of velour warp yarns per given length, has decreased in FIG. 12C, i.e., to a magnitude of zero) when compared to one or both of FIGS. 12A and 12B. Warp yarn 272b" adopts the weave pattern of the base warp yarns circumscribed by border 106"' depicted in FIG. 12C.

Figure 18:
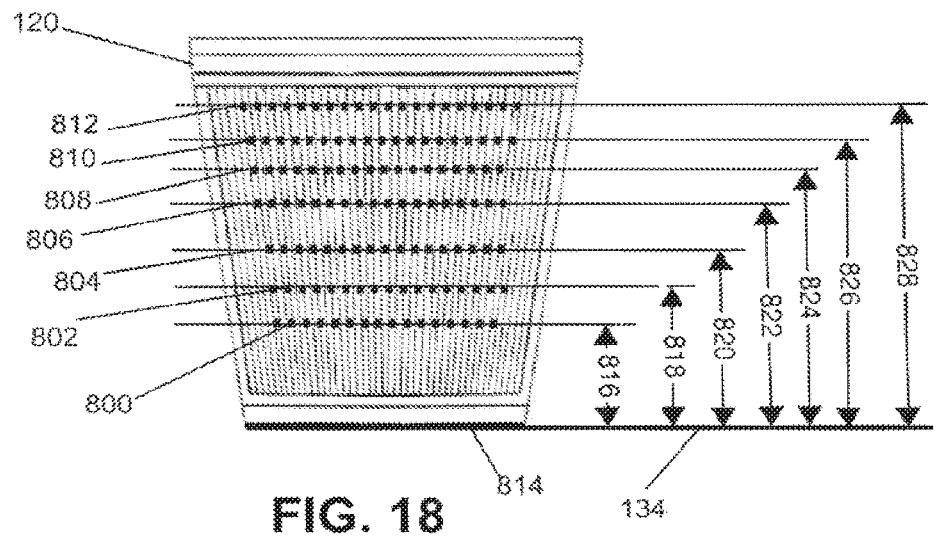
FIG. 18 is a front view of a fan-shaped reed.

The warp yarns are guided by reed 120 through a variety of spacings (or dents) within the reed used to influence the woven width (or diameter) of the prosthesis 10". As illustrated in FIG. 18, the spacings correlate with locations 800, 802, 804, 806, 808, 810, and 812, each location having a different offset (816, 818, 820, 822, 824, 826, and 828) respectively, from a datum 814 on the reed 120. For example, since warp yarn group 250 is shown to enter the base layer first (from the bottom or distal end 20' in FIG. 9), the portion of the prosthesis woven prior to group 250 being moved into the base relates to location 800 of fan shaped reed 120 spaced from a datum 814 on the reed a distance 816. When warp yarn group 250 moves into the base layer, the fan shaped reed moves to a second position causing warp yarns to engage a second location 802 on the fan shaped reed 120, spaced a distance 818 from the datum 814 on the reed. This relationship may continue for the remaining groups 254, 258, 262, 266, and 270 such that portions of the bulbous profile 230' in FIG. 9 can be controllably and repeatably formed.

In order to achieve both a flare and a taper, the process described above to expand the diameter can be reversed while still weaving in the same warp yarn direction. Therefore, warp yarns are shifted from a base layer into a non-base layer such as a velour layer when a taper is desired. The fan shaped reed will therefore be controlled to move in the opposite direction, causing the diameter of the bulbous portion 14' of prosthesis 10' to be reduced, thereby controllably forming the contour 232' illustrated in FIG. 9.

While FIGS. 12A through 12C illustrate a specific behavior of a set of warp yarns applicable to many different woven structures, such as a woven conduit, the principles illustrated in FIGS. 12A through 12C may be replicated throughout portions of woven structures, including woven structures configured to be used as vascular prostheses, e.g., in which complex and varied diameters or contours are desired. Contoured shapes including cylindrical conduits may be formed and configured to represent the natural geometries and shapes of the vascular structure for humans and mammals. This can be accomplished without using yarns of different material attributes, such as shrinking attributes, including coefficients of shrinking. In alternative embodiments however, yarns of different coefficients of shrinking may be used.

Prosthesis 10' of FIG. 8 has a length 220 between twelve and thirty centimeters, although other lengths may be appropriate depending on the intended use. The second tubular portion 16' has a first length 218 greater than ten centimeters, preferably fifteen centimeters, but other lengths may be used. The first tubular portion 12' has a first tubular diameter 222 and a length 212, and the second tubular portion 16' has a second tubular diameter 224. A maximum diameter 226 is greater than the diameters of the first and second tubular portions 12' and 16' respectively, and is positioned within the bulbous portion 14'. The maximum diameter 226 is larger than the diameters 222 and 224 by four to sixteen millimeters, preferably six to ten millimeters, and most preferably by about eight millimeters, but this difference may be varied.

As further illustrated in FIG. 8, the maximum diameter 226 of bulbous portion 14' may be positioned to be closer to a first transition region 22' than a second transition region 24', hence further from the second transition region 24' than the first transition region 22'. For example, the maximum diameter 226 may be positioned at a distance 216 from second transition region 24', such that the distance 216 is between 50% and 75%, or between 60% and 70%, or between 65% and 70% of the length 214 of the bulbous portion 14'. The woven length 214 of the bulbous portion 14' is configured to approximate the diameter 224 within a tolerance of plus or minus two millimeters, preferably one millimeter. The first tubular portion 12' is configured to have a length 212 measured from the first transition region 22' to the proximal end 18', greater or equal to one centimeter. All of these dimensions are provided as examples, for they may vary and are not intended to limit the scope of the invention.

The first transition region 22' represents the transition from the first tubular portion 12' to the bulbous portion 14', while the second transition region 24' represents the transition from the bulbous portion 14' to the second tubular portion 16'. The bulbous portion 14' is woven to have a varied diameter profile and is configurable to have varying degrees of flaring and tapering, to mimic the natural anatomy, shape, dimensions, and intended blood flow dynamics of the aortic root for cardiothoracic surgery pertaining to the ascending aorta.

FIG. 9 illustrates a partial view of a woven prosthesis 10' embodiment representative of elements of the present disclosure, taken about border 240 of FIG. 8. Illustrated in FIG. 9 is a bulbous portion 14', and adjacent thereto portions of the first tubular portion 12' and the second tubular portion 16'. Preferably, the first tubular portion 12' and the second tubular portion 16' have warp yarns continuously woven throughout the bulbous portion 14' into one, preferably both of the first and second tubular portions 12' and 16'. Other elements such as first transition region 22' and second transition region 24' are illustrated as well. The second transition region 24' may correlate with the sinotubular junction common to the anatomy of the ascending aorta.

Optionally, both the first transition region 22' and second transition region 24' may be visually differentiated from other regions of the prosthesis through the use of a diameter transition reference indicator 27', 29'. The diameter transition reference indicator may include the use of a weft yarn of a color different from the color of the weft yarn used in other regions of the prosthesis. For example, the entire prosthesis can be woven with two or more weft yarns of different colors, wherein the color of the weft yarn used for all or a portion of a transition region (e.g., one or both of 22' and 24' in FIG. 9) may be chosen to be a first color while the weft yarn used for the other regions may be chosen from a second color. In an example embodiment, the first color is dark, and is preferably green, blue or even black while the second color is lighter than the dark color, and is optionally white. The second weft yarn can be woven in addition to or instead of a first weft yarn to form the transition reference indicator. The second weft yarn can have an over and under (1/1) interlacing or may optionally float over a plurality of warp yarns. Variations are shown in FIG. 9 as 29' (having two weft passes of a 1/1 interlacing) and 27' (having one weft pass with a plurality of floats). Other arrangements are of course possible and are shown for example in FIGS. 16A, 16B, 17A, and 17B as reference numerals 27" and 29". The diameter transition reference indicators can be used in all embodiments shown within the present application, including those of FIGS. 1, 20-23, 24A, 24B, 25A, and 25B.

In embodiment 10' of FIG. 9, the velour warp yarn density (quantity of velour warp yarns per given length of woven fabric) is shown to decrease when moving towards the maximum diameter portion of the bulbous portion 14', and away from either the first or second transition regions 22' and 24'.

Figure 15:
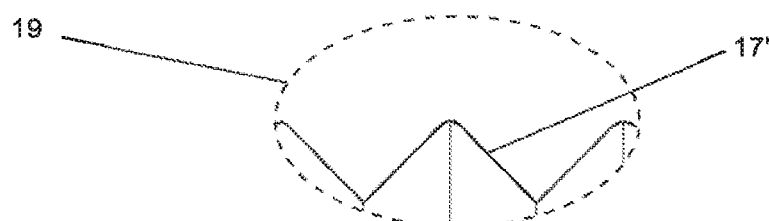
FIG. 15 is a magnified view of a portion of the graft in FIG. 8.

Additionally shown in FIG. 9, the second tubular portion 16' has a crimped surface 17'. This is shown more specifically in FIG. 15, taken about border 19 shown in FIG. 8. The crimped surface can be circularly or helically crimped.

Variations of the shape illustrated in FIG. 9 can be made by controlling how many warp yarns are moved into the base, as well as by controlling the movement and coordination of the fan-shaped reed 120. Additionally, variations can be made by controlling how many weft passes will be woven with the warp yarns while the fan-shaped reed 120 is moving or stationary.

FIG. 11 illustrates the behavior of the velour warp yarns 272b' and 272b" circumscribed by border 244 in FIG. 10. Velour warp yarns 272b' and 272b" are shown to adopt a 5/1 weave pattern in portion 780. The velour warp yarns 272b' and 272b" float over a plurality of weft passes 752 (depicted as yarns extending from left to right in FIG. 11). After floating over weft pass 765 and under weft pass 766, velour warp yarn 272b' is shown to adopt the weave pattern of base layer 60", 60'", which in this example may be represented as a 1/1 weave pattern. Thereafter, velour warp yarn 272b' engages each of the weft passes 769 through 773. Fan shaped reed 120 adjusts from a first position 121' illustrated in FIG. 13A while weaving portion 780 to a second position 121" illustrated in FIG. 13B while weaving a portion at or near transition point 786 (illustrated by a dashed horizontal line). In the first position (FIG. 13A) where the reed 121' has been moved to a top position, warp yarns engage the reed at a low portion 136 of the reed, and in the second position 121" (FIG. 13B), the reed has been moved to a middle position whereby warp yarns engage the reed at the middle portion 134 of the reed 121". Therefore, when velour warp yarn 272b' adopts the base weave pattern 60", 60'", the warp yarn spacing in the base layer 60", 60'" may be maintained.

Further illustrated in FIG. 11, velour warp yarn 272b" is shown to first adopt a 5/1 weave pattern in portion 780 and part of portion 781, and then adopt a weave pattern consistent with the base weave pattern in portion 782. This behavior is similar to that of velour warp yarn 272b', but begins at a different weft pass. After floating over weft pass 766 and under weft pass 767, velour warp yarn 272b" is shown to adopt the weave pattern of a base layer 60'", which in this example may be represented as a 1/1 weave pattern. Similar to velour warp yarn 272b', velour warp yarn 272b" engages each of the weft passes 769 through 773. Fan shaped reed 120 adjusts from a second position 121" illustrated in FIG. 13B to a third position 121'" illustrated in FIG. 13C at or near transition point 788 (illustrated by a dashed horizontal line). In the second position 121" (FIG. 13B), where the reed 121" has been moved to a middle position, warp yarns engage the reed at a middle portion 134 of the reed, and in the third position 121'" (FIG. 13C), the reed 121'" has been moved to a bottom position whereby warp yarns engage the reed 121'" at the top portion 132 of the reed 121'". Therefore, when velour warp yarn 272b" adopts the base weave pattern, the warp yarn spacing in the base layer 60'" may be maintained, and the overall width achieved by the same quantity of warp yarns from portion 780 has increased to increasingly wider portions 781 and 782.

A distance between the two outer most base warp yarns 100 (on the far left) and 92 (on the far right) increases in portion 781 and again in 782 while the woven portion circumscribed by border 244 maintains a fairly consistent warp yarn density.

FIG. 20 illustrates another example embodiment of the present invention. Prosthesis 310 comprises a proximal end 318, and a distal end 320, and a sidewall 330 disposed therebetween, preferably constructed through a weaving process. The sidewall 330 may be woven with a base layer and velour layer, as illustrated by example in FIGS. 12A through 12C. Such weaving processes used to provide prosthesis 310 may be consistent with the weaving of portions of prosthesis 10' described herein.

Prosthesis 310 is configured to have a size and shape in accordance with the bulbous portion of prosthesis 10'. Unlike prosthesis 10', prosthesis 310 does not have first and second tubular portions 12', 16'. Prosthesis 310 may be woven in a manner generally consistent with prosthesis 10'. Prosthesis 310 may be formed, for example, by cutting the bulbous portion 14' from prosthesis 10', and utilizing the woven bulbous portion alone.

FIG. 21 illustrates a prosthesis 410 including a proximal end 418, and a distal end 420, and a sidewall 430 disposed therebetween, preferably constructed through a weaving process. The sidewall 430 may be woven with a base layer and velour layer, as illustrated by example in FIGS. 12A through 12C. Such weaving processes used to provide prosthesis 410 may be consistent with the weaving of portions of prosthesis 10' described herein.

Prosthesis 410 is configured to have a size and shape in accordance with the bulbous portion of prosthesis 10', as well as the first tubular portion 12' of prosthesis 10'. Unlike prosthesis 10', prosthesis 410 does not have a second tubular portion 16'. Prosthesis 410 may be woven in a manner generally consistent with prosthesis 10'. Prosthesis 410 may be formed by removing through cutting for instance, second tubular portion 16' from prosthesis 10', and utilizing the remaining portion of prosthesis 10' not removed.

FIG. 22 illustrates a prosthesis 510 which comprises a proximal end 518, and a distal end 520, and a sidewall 530 disposed therebetween, preferably constructed through a weaving process. The sidewall 530 may be woven with a base layer and velour layer, as illustrated by example in FIGS. 12A through 12C. Such weaving processes used to provide prosthesis 510 may be consistent with the weaving of portions of prosthesis 10' described herein.

Prosthesis 510 is configured to have a size and shape in accordance with the bulbous portion of prosthesis 10', as well as the first tubular portion 12' of prosthesis 10'. Unlike prosthesis 10', prosthesis 510 does not have a second tubular portion 16'. Prosthesis 510 may be woven in a manner generally consistent with prosthesis 10'. Prosthesis 510 may be formed by removing through cutting for instance, second tubular portion 16' from prosthesis 10', and utilizing the remaining portion of prosthesis 10' not removed.

FIG. 23 illustrates a prosthesis 610 which comprises a proximal end 618, and a distal end 620, and a sidewall 630 disposed therebetween, preferably constructed through a weaving process. The sidewall 630 may be woven with a base layer and velour layer, as illustrated by example in FIGS. 12A through 12C. Such weaving processes used to provide prosthesis 610 may be consistent with the weaving of portions of prosthesis 10' described herein.

Prosthesis 610 is configured to have a size and shape in accordance with a portion of the bulbous portion 14' of prosthesis 10', as well as the second tubular portion 16' of prosthesis 10'. Unlike prosthesis 10', prosthesis 610 does not have a first tubular portion 12', nor does it have a proximal portion of the bulbous portion 14' of prosthesis 10'. Therefore, the bulbous portion of prosthesis 610 only expands outward in an increasing diameter configuration, such as a "flared" manner, flaring from the second tubular portion 616 towards the proximal portion 618. Prosthesis 610 may be woven in a manner generally consistent with prosthesis 10'. Prosthesis 610 may be formed by removing through cutting for instance, the proximal portion of the bulbous portion 14', through cutting for instance at the location of the maximum diameter 226 of prosthesis 10' (FIG. 8), as well as the first tubular portion 12' of prosthesis 10', thereby utilizing the remaining portions of prosthesis 10' not removed.

FIGS. 24A and 24B illustrate a prosthesis 910 which comprises a proximal end 918, a distal end 920, and a sidewall disposed therebetween, preferably constructed through a weaving process. The sidewall may be woven with a base layer and velour layer, as illustrated for example in FIGS. 12A through 12C. Such weaving processes used to provide prosthesis 910 may be consistent with the weaving of portions of prosthesis 10' described herein.

Prosthesis 910 is configured to have a flared shape expanding from a minor diameter 938 at the proximal end to a larger diameter at the distal end 920. As illustrated in FIG. 24A, the flared shape of prosthesis 910 is not continuously flared throughout the length 930. Instead, prosthesis 910 has a proximal region 912, a distal region 916, and a flared region 914. The flared region 914 utilizes the weaving technique disclosed throughout this specification and incorporates more warp yarns as velour warp yarns towards the proximal end 918 than towards the distal end 920. The velour density change per unit length within the flared region 914 is greater than one or more adjacent regions 912, 916. For instance, proximal region 912 is shown to have a generally consistent diameter 938 throughout its length 932. Similarly, distal region 916 may have a generally consistent diameter 940 throughout its length 936. The proximal region 912 transitions to the flare region 914 at a proximal transition zone 922, while flared region 926 transitions to the distal region 916 at a distal transition zone 924. In the proximal and distal transition zones 922,924 the rate increase and decrease of the velour warp yarns transitioning to base warp yarns and vice versa is at a maximum. In the flared region 926, the rate of change of velour yarns transitioning to base warp yarns is a constant non-zero value, while in the proximal and distal regions 912 and 916 the rate may be a constant value of zero (representing no change of velour warp yarns to base warp yarns).

FIGS. 25A and 25B illustrate a prosthesis 960 similar to the embodiment of prosthesis 910, but instead the prosthesis 960 has a generally or substantially constant flare between its proximal end 964 and distal end 966. The sidewall of prosthesis 960 may be woven with a base layer and velour layer, as illustrated for example in FIGS. 12A through 12C. Such weaving processes used to fabricate prosthesis 960 may be consistent with the weaving of portions of prosthesis 10' and 910 as described herein.

Prosthesis 960 is configured to have a flared shape expanding from a minor diameter 970 at the proximal end to a larger diameter 972 at the distal end 966. As illustrated in FIG. 25A, the flared shape of prosthesis 910 is continuously flared throughout the length 970. A flared region 962 utilizes the weaving technique disclosed throughout this specification and incorporates more of the total quantity of warp yarns as velour warp yarns towards the proximal end 964 than towards the distal end 966. The velour density therefore steadily decreases within the flared region 962. Throughout the prosthesis along the longitudinal direction a rate of change of velour yarns transitioning to base warp yarns may be a constant non-zero value.

In order to accomplish the change in woven structure width along a weft yarn direction, or for tubular structures, the change in related diameters, the principles of weave pattern adjustment from a velour warp yarn to a base warp yarn, as described previously by example in relation to FIGS. 12A through 12C, and applicable to the finished prostheses illustrated for example in FIGS. 1, 8, 9, 20 through 23, 24A, 24B, 25A, and 25B will be illustrated and further described.

Figure 16B:
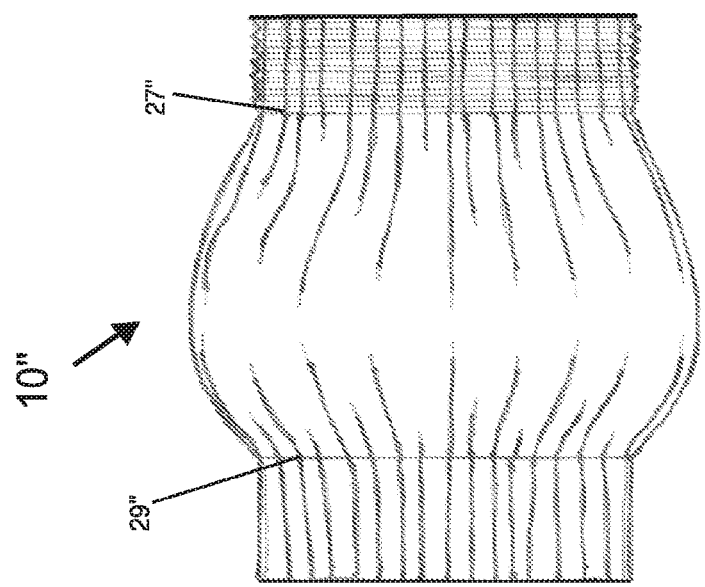
FIG. 16B is an elevation view of the graft of FIG. 16A.
Figure 16A:
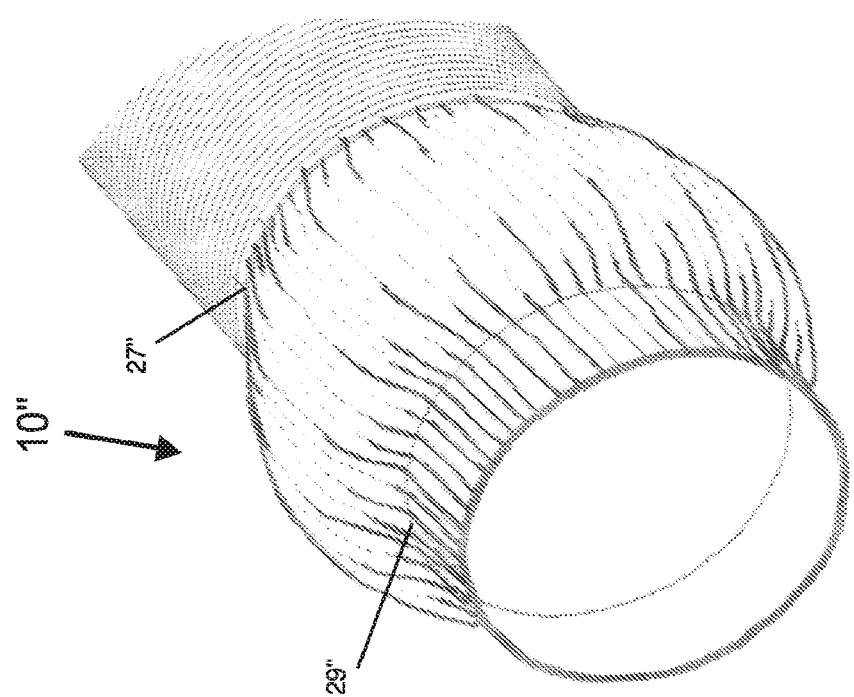
FIG. 16A is a perspective view of a graft according to an example embodiment of the present invention.

It should be noted that embodiments of the invention may involve the movement of all velour warp yarns to the base layer as illustrated for example for prosthesis 10" in FIGS. 16A and 16B prior to emerging from the base layer to return as velour warp yarns. In other embodiments, such as the prosthesis 10''' illustrated in FIGS. 17A and 17B, less than all of the velour warp yarns are moved into the base.

It should also be noted that many permutations of weave patterns may be employed to carry out the invention. For example, warp yarns not in the base may exist in a layer of a three dimensional fabric near or adjacent to the base, and then may be brought into the base. Alternatively, warp yarns not in the base may be of the many varieties of velour warp yarns such as single velour and double velour warp yarns. The single or double velour warp yarns may be brought into the base and adopt a weave pattern involving a higher frequency of interlacing when in the base than when not in the base. This may be fully or partially achieved by the movement of the velour warp yarns from a first position in which the velour warp yarn adopts a velour weave pattern, such as but not limited to a 5/1 velour weave pattern, and adjusts to a second weave pattern, such as a weave pattern consistent with the base, including but not limited to a 1/1, 6/4, or 6/3 weave pattern. Other weave patterns appropriate for the base include, for example, a 3/1 weave pattern, a 2/1 weave pattern, a 1/3 weave pattern, as well as a 1/4 weave pattern.

Additionally, it should be noted that by adjusting where the velour yarns transition into the base, the rate of expansion or contraction for the width of woven structure will be controllable, and enable different shapes and geometries to be fabricated.

Method of Manufacture and Fabrication

Prostheses consistent with and resulting from the methods of manufacture of the embodiments of the present invention may be constructed in a variety of specific ways. In certain embodiments, examples of the present invention may be manufactured in four steps comprising (i) a flat weaving step, (ii) a cutting step, (iii) a heat setting step, and (iv) a sterilization step. The heat setting step may be achieved in a two-step manner, first involving the application of heat through a crimping mandrel to crimp and corrugate certain portions of the surface of portions of the prosthesis, as well as a shaping step in which heat is applied to the prosthesis, whereby the prosthesis takes a "set" or "shape memory" in an expanded state through the usage of an expandable bladder configured to provide a shape consistent with the desired final shape of the prosthesis. Furthermore, an optional step (v) of inserting one or more reference lines at diameter transition regions could be employed. Such a step would demarcate through a change in color of the weft yarn passes at diameter transition regions to enhance the visual identification of such transitions. Such a step may occur through the use of a multi-colored weft insertion mechanism wherein a secondary weft yarn of a different color than the yarn chosen for a primary weft yarn is visually different (colored differently, preferably darker) and used in conjunction with or instead of the primary weft yarn.

Figure 19A:
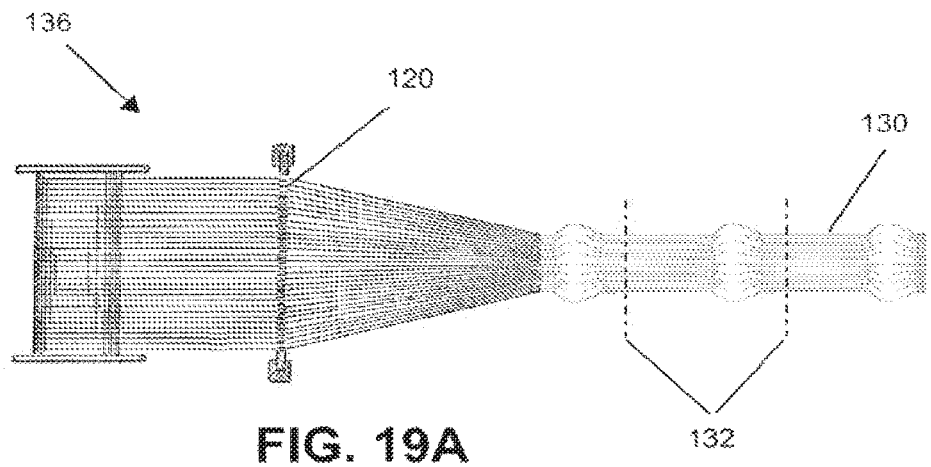
FIG. 19A is an overhead view of a weaving station according to an example embodiment of the present invention.
Figure 19B:
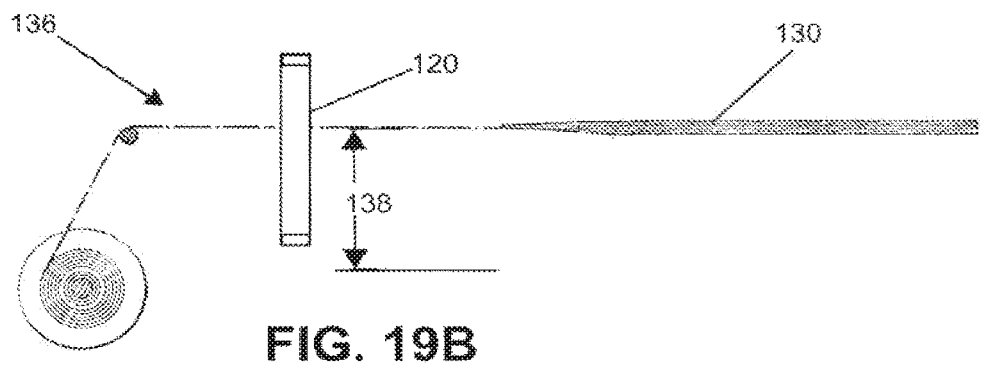
FIG. 19B is a side view of the weaving station of FIG. 19A.

An example prosthesis according to the present invention, including prosthesis 10, 10", 10''', 910, and 960 may be woven with a loom, e.g., a Jacquard-type loom 136, and a warp yarn guide device, e.g., fan-shaped reed 120, as shown in FIGS. 18, 19A, and 19B. The warp yarns or threads (i.e., those yarns extending in the longitudinal direction) and one or more weft or fill yarns or threads (i.e., those yarns extending generally transverse to the longitudinal direction of the portion to be woven) are interlaced with one another in one or multiple predetermined weaving patterns. When weaving a conduit, as employed in various embodiments of the present invention, at the weaving station of the loom, the warp yarns are fed individually through heddles aligned transverse to the longitudinal direction on one of four or more shafts. The upward and downward movement of the shafts moves a preselected pattern of the warp yarns up and then down. In such an arrangement, two of the shafts move the warp yarns for forming the upper surface of the tubular conduit, and two of the shafts move the warp yarns for forming the lower surface of the tubular conduit. As the warp yarns on one shaft are drawn upwardly and the warp yarns on another shaft are drawn downwardly, the weft thread is shuttled in a first direction between those groups of warp yarns to weave the upper surface of the tubular conduit, thereby providing a weft pass of the weft yarn, also known as a machine pick. The weft yarn is then shuttled in a reverse direction between another group of upwardly and downwardly drawn warp yarns to weave the lower surface of the tubular conduit, thereby creating an additional weft pass or machine pick. The position of the shafts and thus the position of the warp yarns is then reversed and the weft thread is again shuttled between the groups of warp yarns, creating a plurality of weft passes, wherein the process continues resulting in a woven tubular shape.

As they approach the weaving station, the warp yarns are fed between the fingers of a fan-shaped reed 120, which aligns the yarns for weaving and which thus determines the ultimate shape of the woven article. Whereby weaving tubular articles having a substantially constant diameter is performed utilizing a conventional front reed which is fixed in place and which has evenly spaced fingers used to produce constant spacing between the warp yarns, reeds with varying spacing will be beneficial for carrying out the present invention but are not required. An example of such a reed has spacing between the fingers which is narrow at a first end or bottom end, and gradually increases toward the top end. In contrast to conventional reeds, the fan-shaped reed 120 is not held in a fixed position, but rather is moved upward or downward with respect to the warp yarns to alter yarn to yarn spacing in all or portions of the of the article being woven. For example, fan shaped reed 120', 120". 120''', as shown in FIGS. 14A-14C, may be moved upwards and downwards, causing warp yarns to engage the fan shaped reed 120', 120", 120''' at a plurality of elevations represented by dimensions 816 through 828 in FIG. 18, all with respect to a datum 134. When the fan shaped reed is at its highest position, the warp yarns engage the reed at a low position such as that represented by location 800 in FIG. 18. Likewise, when the fan shaped reed is at its lowest position, the warp yarns engage the reed at a high location such as that represented by location 812 in FIG. 18. In the context of fabricating a tubular article consistent with certain embodiments of the present disclosure, the movement of the fan-shaped reed 120 provides for an adjustable diameter.

When programmed to coordinate with the specific manipulation or engagement of warp yarns, the spacing of warp yarns can be adjusted to provide for sufficient space such that one or more velour warp yarns may be brought into the base, and woven as a part of the base, thereby adopting a weave pattern consistent with the base. The invention thereby enables a base warp yarn density to be held within a range or otherwise managed, such that the diameter of a tubular woven conduit may be selectively adjusted, without requiring an adjustment of the finished spacing of warp yarns within a base layer. Provided that a sufficient quantity of velour warp yarns are able to be brought into the base, controlled flaring and tapering of all or portions of a woven tubular conduit may therefore be provided When the reed 120 is gradually moved upwards as the weaving of the tubular conduit advances, the spacing between the warp yarns and, hence, the diameter of the tubular article being woven, see, e.g., greige 130 in FIG. 19A, will gradually be decreased. Similarly, when the reed 120 is gradually moved downward as the weaving of the tubular conduit advances, the spacing between the warp yarns will increase as will the diameter of the tubular article being woven. The rate of movement of the reed 120 will determine the taper of the article being woven. The faster the reed is moved, the larger the angle of taper, and the slower the reed is moved, the smaller the angle of taper. Moving the reed at a constant rate will produce a constant angle of taper. However, changing the rate of movement of the reed enables tubular articles to be formed with curved or changing angles of taper. It is noted that use of the reed is not required as the spacing between warp yarns may already be large enough to accommodate shifting of the non-base warp yarns, e.g., velour war yarns, into the base layer of the prosthesis.

When using a movable reed 120, it is initially held in a fixed lower position to weave a substantially uniform diameter tubular conduit. When a desired length of the tubular conduit has been reached, the reed 120 is drawn downwards in increments, providing additional spacing between certain warp yarns such that additional warp yarns may be moved from a first position in a velour layer to a second position in the base layer. This is done such that when the warp yarns are brought into the base layer, and adopt a weave pattern consistent with the base layer, as illustrated in FIGS. 12B-12C, for example, the resulting spacing between the warp yarns adjacent the additional warp yarn is increased. With each change for additional warp yarns to be brought into the base, the movement of the reed 120 will have to be evaluated to see if an adjustment is needed to provide sufficient spacing such that at a rate which would produce the desired angle of taper. The front reed is continued to be drawn downward as the weaving process continues until a woven fabric having the desired tubular configuration has been formed as the greige 130 represented for example in FIGS. 19A and 19B.

The weaving step utilized to fabricate embodiments of the present invention may be conducted for a given length of a woven structure. In accordance with embodiments of the present invention, a plurality of bulbous portions may be woven into a greige 130 shown in FIGS. 19A and 19B. A secondary cutting step may be employed at cutting locations 132 shown in FIG. 19A as dashed lines in order to section the woven structure to a length consistent with the desired intended usage of a prosthesis.

During further processing of the prosthesis, all or portions of the prosthesis of the present invention may be crimped to provide for "self-supporting" qualities of the finished prosthesis, adding rigidity to the tubular prosthesis wherein the strength is needed to ensure proper cross sectional area for assured flow of blood through the conduits. Examples are disclosed by example in U.S. Pat. No. 3,945,052 herein incorporated by reference. As illustrated in all the figures, neither the bulbous portion nor the collar or first woven portion 12, 12' are crimped but they may be crimped in other embodiments. A benefit to not crimping these sections include, for example, being able to provide a surgeon locally flat or slightly curved surfaces beneficial for anastomosis and suturing. Providing a surface that has crimps, pleats, or corrugations in the bulbous portion 14, 14' and/or a collar, e.g., the proximal tubular woven portion 12, 12', may complicate suturing and anastomosis procedures as it is understood to be more convenient to suture and perform a proximal anastomosis on a flat or slightly curved surface rather than a non-uniform crimped, pleated, or corrugated surface.

The woven fabric or prosthesis 10, 10', 10'', 10''', 910, 960 may be coated with a collagen or gel coating applied to entire length of the prosthesis for sealing purposes. Therefore, in addition to a uniform textile structural porosity capable of being achieved in a base layer (between warp yarns, weft yarns, and interwoven combinations thereof), a uniform functional porosity impacting permeability of the woven fabric to a fluid may additionally be achieved.

The prosthesis 10, 10', 10'', 10''', 910, 960 may be sterilized from any of the sterilization process suitable for woven grafts, including gamma radiation or cobalt 60 radiation, ethylene oxide gas, or e-beam radiation as commonly known to one skilled in the art.

Materials useful for forming embodiments of the present invention include textile weaving products, for example, synthetic materials such as synthetic polymers. Synthetic yarns suitable for use in the present invention include, but are not limited to, polyesters, including polyethylene terephthalate polyesters (herein referred to as PET), polypropylenes (herein referred to as PP), polyethylenes, polyurethanes and polytetrafluoroethylenes (herein referred to as PTFE). The yarns may be of the monofilament, multifilament, spun type or combinations thereof. The yarns may also be flat, twisted or textured, and may have high, low or moderate shrinkage properties. Such yarn materials, for instance PET, are available from DuPont under the trade name of Dacron. The yarns may, for example, have a total denier in the range of 15 to 300, or in the range 100 to 200, and may also be about 140 denier but can have other sizes as well. The yarns may be comprised of single or multiple plies. An example yarn that may be utilized according to the present invention may be texturized and PET based, and comprises two plies, each having a denier of 70, the yarn having a total denier of 140.

The following four examples are to be illustrative of embodiments that relate to the present invention. The first two relate to the formation of a bulbous prosthesis, consistent with prosthesis 10, 10' shown in FIGS. 1 and 8 respectively. The second two relate to the formation of a prosthesis tapering generally from a small diameter end to a larger diameter end. Unless otherwise noted, the vascular prosthesis of all of the following examples were fabricated through flat-woven processes, arranged to achieve a tubular configuration using an electronic Jacquard weaving machine and a variable reed such as a fan-shaped reed.

Example 1

In a first example of the present invention, an aortic prosthesis is constructed to have small diameter of approximately 32 millimeters, and a maximum diameter of approximately 40 millimeters. The prosthesis is constructed in accordance with the elements represented for instance in FIGS. 1 and 8.

A weft yarn material chosen for the present example is comprised of polyethylene terephthalate (PET) and is configured from two plies of 70 denier per ply, thereby having a final denier of 140. A warp yarn material chosen for the present example is comprised of polyethylene terephthalate (PET) and is configured from two plies of 70 denier per ply, thereby having a final denier of 140. Either or both of the warp and weft yarn materials may be texturized or untexturized. A base weave pattern is chosen to be a plain weave pattern. It is determined that a velour layer will be woven to the outside of the base layer. The weave pattern chosen for the velour layer is a 5/1 pattern.

A constant weft yarn spacing is chosen to be used for the weaving of all woven portions of the prosthesis. Specifically, an average weft yarn spacing (or density) of 66 yarns per inch (26 weft yarns per centimeter) is determined to be used for all woven portions of the prosthesis. Although a goal spacing of 66 yarns per inch is chosen, one will appreciate that tolerances throughout the woven prosthesis will be expected. Preferably, such a spacing will be within a range of plus or minus 30% of the targeted average, more preferably 20% of the targeted average, and most preferably 10% of the targeted average.

A total quantity of warp yarns is chosen based on a desired warp yarn density, positioning, and finished diameters, including the maximum diameter portion of the woven article. By way of example, a total of 703 warp yarns have been chosen.

When weaving the first portion 12, 12' and the third portions 16, 16' (both collar and crimped/corrugated sections respectively), the position of the reed 120 is set to its narrowest width in order to achieve a woven fabric tubular diameter of approximately 32 mm (or flat width 50.3 mm), and the total of 703 warp yarns are so divided into two groups. The first group includes 469 warp yarns to form the base layer, and the second group includes 234 warp yarns to form the velour layer of the first portion. Therefore, to achieve the intended tubular diameter of 32 millimeters, the warp spacing for the base layer is 118 yarns per inch (46 yarns per centimeter) when a 32 millimeter diameter portion is to be woven, and 59 velour warp yarns per inch (23 yarns per centimeter) for the velour layer. The average fabric warp spacing including both velour and base warp yarns is the sum of both layers, i.e., 177 yarns per inch (70 yarns per centimeter). The first tubular portion 12, 12' is woven with warp yarns acting as both base warp yarns and velour warp yarns to establish the first tubular portion 12, 12'.

The fan shaped reed 120 is gradually repositioned in steps during the weaving process to achieve the desired profile of the bulbous portion 14, 14'. This occurs in combination with the conversion of velour warp yarns into base warp yarns, until the maximum desired diameter is achieved.

When reaching the maximum diameter portion, the reed 120 is at its widest to help fabricate the maximum fabric tubular diameter of 40 mm (or flat width 62.8 mm), and the total of 703 warp yarns are so divided into two groups that 584 yarns now form the fabric base layer (for example, the inner surface), and 119 yarns form the velour layer or layers. As a result, the warp spacing for the ground layer 60, 60' is maintained as 118 yarns per inch (46), while the velour layer is reduced to 24 yarns per inch (9 yarns per centimeter) for the velour layer 62, 62".

Example 2

In a second example of the present invention, an aortic prosthesis is constructed to have small diameter of approximately 24 millimeters, and a maximum diameter of approximately 32 millimeters. The prosthesis is constructed in accordance with the elements represented for instance in FIGS. 1 and 8.

A weft yarn material chosen for the present example is comprised of polyethylene terephthalate (PET) and is configured from two plies of 70 denier per ply, thereby having a final denier of 140. A warp yarn material chosen for the present example is comprised of polyethylene terephthalate (PET) and is configured from two plies of 70 denier per ply, thereby having a final denier of 140. Either or both of the warp and weft yarn materials may be texturized or untexturized. A base weave pattern is chosen to be a plain weave pattern. The velour layer 62, 62" can be woven to the outside of the base layer 60, 60'. The weave pattern chosen for the velour layer is a 5/1 pattern.

A constant weft yarn spacing is chosen to be used for the weaving of all woven portions of the prosthesis 10, 10'. Specifically, a weft yarn spacing (or density) of 66 yarns per inch (26 weft yarns per centimeter) is determined to be used for all woven portions of the prosthesis 10, 10'. Although a goal spacing of 66 yarns per inch is chosen, one will appreciate that tolerances throughout the woven prosthesis will be expected. Preferably, such a spacing will be within a range of plus or minus 30% of the targeted average, more preferably 20% of the targeted average, and most preferably 10% of the targeted average.

A total quantity of warp yarns is chosen based on a desired warp yarn density, positioning, and finished diameters, including the maximum diameter portion of the woven article. By way of example, a total of 550 warp yarns have been chosen.

When weaving the first portion 12, 12' and the third portion 16, 16' (both corrugated and collar portions), the position of the reed 120 is set to narrowest width in order to achieve a woven fabric tubular diameter of approximately 24 mm (or flat width 37.7 mm), and the total of 550 warp yarns are so divided into two groups. The first group includes 367 warp yarns to form the base layer 60, 60', and the second group includes 183 warp yarns to form the velour layer 62, 62' of the first portion 12, 12'. Therefore, to achieve the intended tubular diameter of 24 millimeters, the warp spacing for the base layer 60, 60' is 124 yarns per inch (49 yarns per centimeter) when a 24 millimeter diameter portion is to be woven, and 62 velour warp yarns per inch (24 yarns per centimeter) for the velour layer 62, 62'. The average fabric warp spacing including both velour and base warp yarns is the sum of both layers, (i.e., 177 yarns per inch, or 70 yarns per centimeter). The first tubular portion 12, 12' is woven with warp yarns acting as both base warp yarns and velour warp yarns to establish the first tubular portion 12, 12'. Again, the reed 120 is gradually repositioned in steps during the weaving process to achieve the desired profile of the bulbous portion 14, 14'. This occurs in combination with the conversion of velour warp yarns into base warp yarns, until the maximum desired diameter is achieved.

When reaching the maximum diameter portion, the reed 120 is at its widest to help achieve the maximum fabric tubular diameter of 32 mm (or flat width 50.3 mm), and the total of 550 warp yarns are so divided into two groups that 491 yarns now form the fabric base layer 60, 60' (for example, the inner surface), and 59 yarns form the velour layer or layers 62, 62'. As a result, the warp spacing for the ground layer 60, 60' is maintained as 124 yarns per inch (49 yarns per centimeter), while the velour layer 62, 62" is reduced to 15 yarns per inch (6 yarns per centimeter) for the velour layer.

After the maximum desired diameter is achieved, the diameter of the prosthesis 10, 10' is intentionally reduced or tapered by reversing the steps used to create the increased diameter. Specifically, warp yarns now in the base 60, 60' of the prosthesis 10, 10' are adjusted and moved out of the base 60, 60' to behave and perform as velour warp yarns. The spacing of the base warp yarns still within the base 60, 60' are adjusted to accommodate the removal of the warp yarn from the base layer 60, 60' to the velour layer 62, 62', without significantly impacting the warp yarn spacing within the base 60, 60'.

Example 3

In a third example of the present invention, an aortic prosthesis is constructed to have a small diameter of approximately 12 millimeters, and a maximum diameter of approximately 36 millimeters. The prosthesis is constructed in accordance with the embodiments represented for instance in FIGS. 24A and 24B.

A 40 denier/27 filament flat yarn with 5 twists per inch comprised of polyethylene terephthalate (PET) is chosen for both the weft yarn and warp yarns of the present example. Either or both of the warp and weft yarn materials may be texturized or untexturized. A base weave pattern is chosen to be a plain weave pattern. It is determined that two velour layers will be woven on both sides of the base layer. One of the velour layers will be an interior velour layer and the other will be an exterior velour layer. The weave pattern chosen for the velour layers is a 5/1 pattern.

A generally constant weft yarn spacing is chosen to be used for the weaving of all woven portions of the prosthesis. Specifically, a weft yarn spacing of 160 yarns per inch (63 weft yarns per centimeter) is determined to be used for all woven portions of the prosthesis. Although a goal spacing of 160 yarns per inch is chosen, one will appreciate that tolerances throughout the woven prosthesis will be expected. Preferably, such a spacing will be within a plus or minus range of 30% of the targeted average, more preferably 20% of the targeted average, and most preferably 10% of the targeted average.

A total quantity of warp yarns to be continuously woven throughout the prosthesis is chosen based on a desired warp yarn density, positioning, and finished diameters, including the maximum diameter portion of the woven article. By way of example, a total of 890 warp yarns (ends) has been chosen.

The total of 890 warp yarns are so divided into three groups. The three groups of correspond to the base layer (e.g., 296 warp yarns), the interior velour layer (e.g., 297 warp yarns), and the exterior velour layer (e.g., 297 warp yarns). At the small diameter region 912, a warp spacing for each of the base, interior, and exterior layers is chosen to be 200 yarns per inch (79 yarns per centimeter). The average fabric warp spacing including all velour and base warp yarns (i.e., the total warp yarn density) is the sum of the three layers i.e., 600 yarns per inch (236 yarns per centimeter). Although a goal spacing of 200 yarns per inch is chosen for the starting base and velour layers, one will appreciate that tolerances throughout the woven prosthesis will be expected. Preferably, such a spacing will be within a plus or minus range of 30% of the targeted average, more preferably 20% of the targeted average, and most preferably 10% of the targeted average.

When weaving the first proximal portion 912 the position of the reed 120 is set to its narrowest width (highest elevation) in order to achieve a woven fabric tubular diameter of approximately 12 mm (or flat width 19.4 mm). The first proximal tubular portion 912 is woven for a length 932 of approximately 10 centimeters. After the first section 912 is woven, the weaving is adjusted at a proximal transition region to adjust the diameter to a flared region 914. To accomplish this velour warp yarns in either or preferably both the interior and exterior velour layers are gradually transitioned into the base layer. This is accomplished in a gradual manner and in conjunction with the gradual moving and repositioning of the reed 120 such that an increased spacing of the base warp yarns can be achieved to provide space for velour yarns to be woven into the base, and therefore adopt a base weave pattern. The loom is programmed such that the warp yarn density within the base layer stays generally constant while the velour warp yarn densities in one or both of the interior and exterior velour layers gradually decreases. This occurs for a length of approximately 5 centimeters until the maximum diameter 940 is achieved at the distal transition region distal 924. Thereafter, a region 916 of generally constant diameter is to be formed.

When reaching the distal end 966 wherein the diameter 940 is greatest, the reed 120 is at its widest to help achieve the maximum fabric tubular diameter of 36 mm (or flat width 56 mm), and the total of 890 warp yarns are no longer required to be moved from the velour layer to the base layer. Assuming all velour warp yarns have been moved into the base layer, the velour warp yarn density will be zero while the base warp yarn density will be 200 yarns per inch. The distal portion 916 can be woven for a length 936 of 10 centimeters thereby producing a finished length of 25 centimeters for the entire prosthesis.

This third example can therefore produce a flared woven prosthesis having substantially cylindrical proximal 912 and distal 914 diameters and a transition or flare region 914 interposed therebetween. Throughout all regions a base layer warp yarn density can be maintained generally constant and within the tolerances mentioned previously (i.e., plus or minus 30% of the targeted average, more preferably 20% of the targeted average, and most preferably 10% of the targeted average). A sample listing of the parameters associated with this third example as they exist along reference datums a through h in FIG. 24A is shown in FIG. 26 as table 911.

Example 4

In a fourth example of the present invention, an aortic prosthesis is constructed to have small diameter of approximately 12 millimeters, and a maximum diameter of approximately 36 millimeters. The prosthesis is constructed in accordance with the embodiments represented for instance in FIGS. 25A and 25B.

A 40 denier/27 filament flat yarn with 5 twists per inch comprised of polyethylene terephthalate (PET) is chosen for both the weft yarn and warp yarns of the present example. Either or both of the warp and weft yarn materials may be texturized or untexturized. A base weave pattern is chosen to be a plain weave pattern. It is determined that two velour layers will be woven outside of the base layer. One of the velour layers will be an interior velour layer and the other will be an exterior velour layer. The weave pattern chosen for the velour layers is a 5/1 pattern.

A generally constant weft yarn spacing of 160 yarns per inch (63 weft yarns per centimeter) is chosen to be used for the weaving of all woven portions of the prosthesis. Although a goal spacing of 160 yarns per inch is chosen, one will appreciate that tolerances throughout the woven prosthesis will be expected. Preferably, such a spacing will be within a range plus or minus 30% of the targeted average, more preferably 20% of the targeted average, and most preferably 10% of the targeted average. A total quantity of warp yarns to be continuously woven throughout the prosthesis is chosen based on a desired warp yarn density, positioning, and finished diameters, including the maximum diameter portion of the woven article. By way of example, a total of 890 warp yarns (ends) has been chosen.

The total of 890 warp yarns are so divided into three groups. The three groups correspond to the base layer (e.g., 296 warp yarns), the interior velour layer (e.g., 297 warp yarns), and the exterior velour layer (e.g., 297 warp yarns). At the proximal end 964, a warp spacing for each of the base, interior, and exterior layers is chosen to be 200 yarns per inch (79 yarns per centimeter). The average fabric warp spacing including all velour and base warp yarns (i.e., the total warp yarn density or spacing) is the sum of the three layers, i.e., 600 yarns per inch (236 yarns per centimeter).

The prosthesis has a flared configuration in which the diameter is generally always increasing from the proximal end 964 towards the distal end 966. The prosthesis can further be represented to have a smaller diameter portion 968 and a larger diameter portion 974.

To accomplish the enlargement of diameters through weaving, velour warp yarns in either or preferably both the interior and exterior velour layers are gradually transitioned into the base layer in conjunction with a gradual repositioning of fan shaped reed 120 to increase the spacing between base warp yarns by lowering the reed. The velour yarns are woven into the base, and therefore adopt a base weave pattern, or at least a higher degree of interlacing with respect to weft yarn passes.

The loom is programmed such that the warp yarn density within the base layer stays generally constant while the velour warp yarn densities in one or both of the interior and exterior velour layers gradually decreases. This occurs for the entire length 970 (approximately 25 centimeters) until the maximum diameter 972 is achieved at the distal end 966.

When reaching the distal end 966 wherein the diameter is greatest, the reed 120 is at its widest to fabricate the maximum fabric tubular diameter of 36 mm (or flat width 62.8 mm), and the total of 890 warp yarns are no longer required to be moved from the velour layer to the base layer. Assuming all velour warp yarns have been moved into the base layer, the velour warp yarn density will be zero while the base warp yarn density will be 200 yarns per inch.

This example can therefore produce a flared woven prosthesis having substantially gradual transition or flare region 962 throughout. Throughout all regions a base layer warp yarn density can be maintained generally constant and within the tolerances mentioned previously (i.e., 30% of the targeted average, preferably 20% within the targeted average, and most preferably within 10% of the targeted average). A sample listing of the parameters associated with this fourth example as they exist along reference datums a through f of FIG. 25A is shown in FIG. 27 as table 961.

As many apparently widely different embodiments of the present invention can be made without departing from the spirit and scope thereof, it is to be understood that the invention is not limited to the specific embodiments thereof except as defined in the appended claims.

The invention claimed is:

1. An implantable medical prosthesis comprising:
   a woven base comprising base warp yarns interwoven with weft yarn passes, the woven base at least partially forming smaller and larger diameter portions of the prosthesis; and
   one or more velour yarns forming part of both the smaller and larger diameter portions;
   wherein in at least a portion of the larger diameter portion at least one of the one or more velour yarns incorporated into the woven base exhibits a weave pattern consistent with the woven base;
   wherein the larger diameter portion is not crimped.

2. The implantable medical prosthesis of claim 1, wherein within the smaller diameter portion, the at least one of the one or more velour yarns is not incorporated into the woven base and does not exhibit a weave pattern consistent with the woven base.

3. The implantable medical prosthesis of claim 1, wherein a spacing between the base warp yarns is maintained approximately the same in the smaller and larger diameter portions without adding additional warp yarns to the larger diameter portion beyond that in the smaller diameter portion.

4. The implantable medical prosthesis of claim 1, wherein an increase in diameter of the prosthesis going from the smaller diameter portion to the larger diameter is effected by increasing spacing between the base warp yarns during weaving of the prosthesis.

5. The implantable medical prosthesis of claim 1, wherein the spacing between the base warp yarns in the larger diameter portion is made smaller without reducing a diameter of the larger diameter portion by at least one of the one or more velour yarns incorporated into the woven base of the larger diameter portion.

6. The implantable medical prosthesis of claim 1, wherein the prosthesis is a generally tubular graft and the larger diameter portion lies within a portion of the graft varying in diameter along a longitudinal axis of the graft and the smaller diameter portion lies within a portion of the graft having a generally uniform diameter.

7. The implantable medical prosthesis of claim 1, wherein the prosthesis is a generally tubular graft and the larger and smaller diameter portions lie within a portion of the prosthesis in diameter along a longitudinal axis of the graft.

8. The implantable medical prosthesis of claim 1, wherein in at least a portion of the smaller diameter portion the one or more velour yarns exhibit a float that is entirely absent or smaller in the larger diameter portion.

9. The implantable medical prosthesis of claim 1, wherein a spacing between the base warp yarns in the smaller diameter portion is within 30% of the size of the spacing in the larger diameter portion.

10. The implantable medical prosthesis of claim 1, wherein a quantity of the base warp yarns and velour yarns is the same in the larger diameter portion as the smaller diameter portion, and wherein the base warp yarns and the velour warp yarns are continuously woven between the smaller diameter portion and the larger diameter portion.

11. The implantable medical prosthesis of claim 1, wherein the prosthesis comprises a secondary woven layer disposed over at least one of the smaller and larger diameter portions, and wherein a portion of a yarn forming the secondary layer is incorporated into the base layer of the larger portion.

12. The implantable medical prosthesis of claim 1, wherein a spacing between the base warp yarns in the smaller diameter portion is within 20% of the size of the spacing in the larger diameter portion.

13. The implantable medical prosthesis of claim 1, wherein a spacing between the base warp yarns in the smaller diameter portion is within 10% of the size of the spacing in the larger diameter portion.

* * * * *